(12) United States Patent
Levin

(10) Patent No.: US 12,127,902 B2
(45) Date of Patent: Oct. 29, 2024

(54) SCAFFOLDS, SYSTEMS, METHODS, AND COMPUTER PROGRAM PRODUCTS FOR REGENERATING A PULP

(71) Applicant: Martin David Levin, Bethesda, MD (US)

(72) Inventor: Martin David Levin, Bethesda, MD (US)

( * ) Notice: Subject to any disclaimer, the term of this patent is extended or adjusted under 35 U.S.C. 154(b) by 976 days.

(21) Appl. No.: 16/644,636

(22) PCT Filed: Sep. 7, 2018

(86) PCT No.: PCT/US2018/050060
§ 371 (c)(1),
(2) Date: Mar. 5, 2020

(87) PCT Pub. No.: WO2019/051298
PCT Pub. Date: Mar. 14, 2019

(65) Prior Publication Data
US 2021/0059787 A1    Mar. 4, 2021

Related U.S. Application Data

(60) Provisional application No. 62/555,703, filed on Sep. 8, 2017.

(51) Int. Cl.
| | |
|---|---|
| *A61C 5/50* | (2017.01) |
| *A61C 13/00* | (2006.01) |
| *A61K 6/54* | (2020.01) |
| *G06T 17/00* | (2006.01) |

(52) U.S. Cl.
CPC ............ *A61C 5/50* (2017.02); *A61C 13/0003* (2013.01); *A61C 13/0004* (2013.01); *A61K 6/54* (2020.01); *G06T 17/00* (2013.01)

(58) Field of Classification Search
None
See application file for complete search history.

(56) References Cited

U.S. PATENT DOCUMENTS

| | | | |
|---|---|---|---|
| 4,565,722 A | 1/1986 | Highgate et al. | |
| 6,264,471 B1 | 7/2001 | Martin | |
| 7,210,935 B2 | 5/2007 | Highgate et al. | |
| 9,138,299 B2 * | 9/2015 | Van Lierde ............ | G16H 50/50 |
| 9,492,360 B2 | 11/2016 | Jia et al. | |
| 2002/0168615 A1 | 11/2002 | Kimmel | |
| 2004/0248067 A1 | 12/2004 | Lopez et al. | |
| 2004/0265783 A1 | 12/2004 | Karmaker et al. | |
| 2005/0079470 A1 | 4/2005 | Rutherford et al. | |
| 2010/0092923 A1 | 4/2010 | Stites | |
| 2011/0020310 A1 | 1/2011 | Nakashima et al. | |
| 2012/0065943 A1 | 3/2012 | Fisker et al. | |
| 2013/0171580 A1 | 7/2013 | Van Lierde et al. | |
| 2013/0209961 A1 | 8/2013 | Rubbert et al. | |
| 2013/0209965 A1 | 8/2013 | Fisker et al. | |
| 2014/0147815 A1 | 5/2014 | Sicurelli et al. | |
| 2014/0229145 A1 * | 8/2014 | Van Lierde ........ | A61C 13/0004 703/1 |
| 2014/0302111 A1 * | 10/2014 | Mao ........................ | A61L 27/12 514/8.4 |
| 2015/0289955 A1 * | 10/2015 | Guggenmos ............ | A61C 13/08 433/29 |
| 2016/0045282 A1 | 2/2016 | Levin | |
| 2017/0203009 A1 * | 7/2017 | Yang ........................ | A61L 27/18 |
| 2017/0262978 A1 * | 9/2017 | Reynolds ................ | A61B 6/032 |

FOREIGN PATENT DOCUMENTS

| | | |
|---|---|---|
| CN | 101803958 A | 8/2010 |
| CN | 103083094 A | 5/2013 |
| WO | 2009055609 A1 | 4/2009 |
| WO | 2013181105 A1 | 12/2013 |
| WO | 2014115090 A1 | 7/2014 |
| WO | 2016025587 A1 | 2/2016 |

OTHER PUBLICATIONS

International Search Report and Written Opinion of the International Searching Authority for International Application No. PCT/US2018/050060, European Patent Office (EPO), Rijswijk, dated Jan. 7, 2019, 13 pages.
Gutmann et al., "Root Canal Obturation: An Update," Academy of General Dentistry, not dated, 11 pages, date: Jan. 28, 2014.
Barborka et al., "Long-term Clinical Outcome of Teeth Obturated with Resilon," Journal of Endodontics, vol. 43, No. 4, Apr. 2017, pp. 556-560.
Cetenovic et al., "Biocompatibility Investigation of New Endodontic Materials Based on Nanosynthesized Calcium Silicates Combined with Different Radiopacifiers," Journal of Endodontics, vol. 43, No. 3, Mar. 2017, pp. 425-432.
William Cheung, "A review of the management of endodontically treated teeth: Post, core and the final restoriation," Journal of American Dental Association (JADA), vol. 136, May 2005, pp. 611-619.
Vibha Hegde and Shashank Arora, "Sealing ability of a novel hydrophilic vs. conventional hydrophobic obturation systems: A bacterial leakage study," Journal of Conservative Dentistry, vol. 18, No. 1, Jan.-Feb. 2015, pp. 62-65.
Li et al., "Ability of New Obturation Materials to Improve the Seal of the Root Canal System—A Review," Acta Biomaterialia, vol. 10, No. 3, Mar. 2014, pp. 1050-1063.
Shweta Tekriwal and Aniket Kumar, "Comparative Evaluation of Volumetric Changes of Propoint Obturating System: An In Vitro Study," Annals of International Medical and Dental Research, vol. 3, No. 4, May 2017, pp. 9-12.

(Continued)

*Primary Examiner* — Lori A. Clow
(74) *Attorney, Agent, or Firm* — Sterne, Kessler, Goldstein & Fox P.L.L.C.

(57) ABSTRACT

A scaffold for regenerating a pulp of a root canal includes a body that has a pre-formed contour that closely matches a contour of the root canal. A method of making a customized regenerative scaffold includes generating a three-dimensional image of a root canal. The method also includes manufacturing the customized regenerative scaffold based on the three-dimensional image of the root canal.

22 Claims, 22 Drawing Sheets

(56) References Cited

OTHER PUBLICATIONS

Chiu et al., "The Characteristics of Mineral Trioxide Aggregate/Polycaprolactone 3-dimensional Scaffold with Osteogenesis Properties for Tissue Regeneration," Journal of Endodontics, vol. 43, No. 6, dated Apr. 4, 2017, DOI: 10.1016/j.joen.2017.01.009, 7 pages.

* cited by examiner

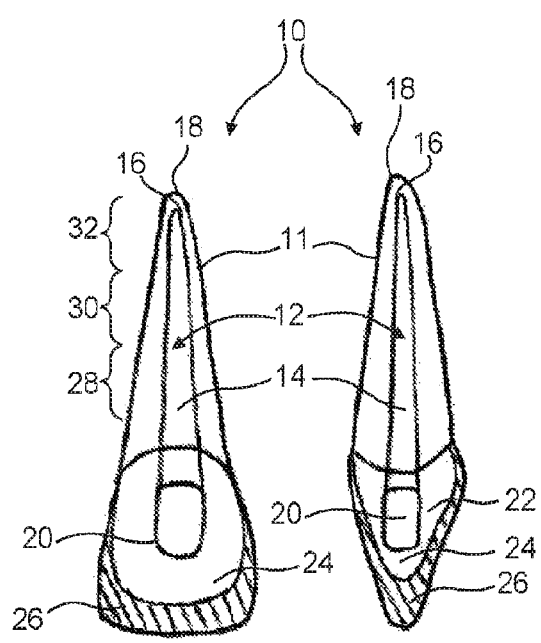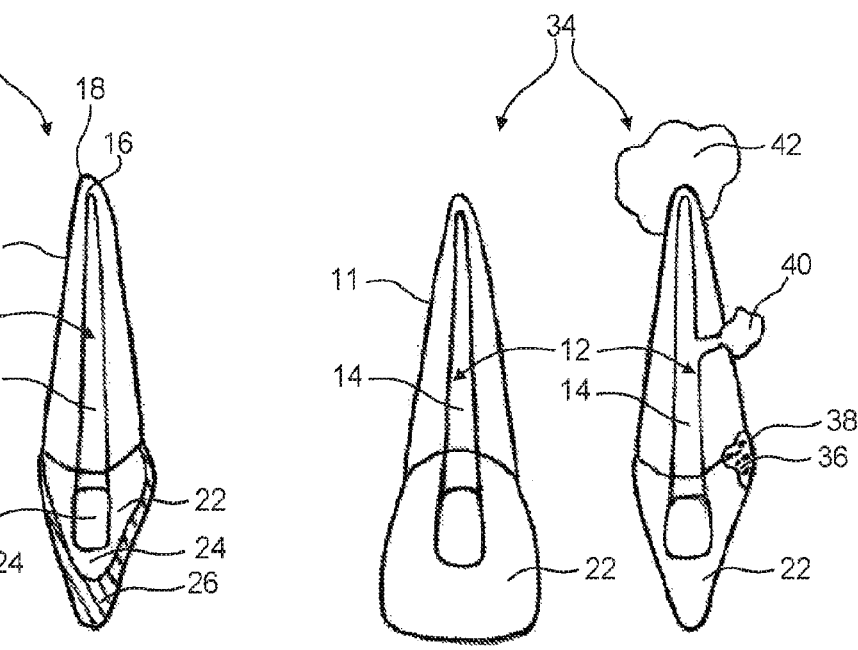
FIG. 1A    FIG. 1B    FIG. 2A    FIG. 2B

| Test | Tooth #8 | Tooth #9 | Tooth #10 |
|---|---|---|---|
| Percussion | Normal | +++ | Normal |
| Palpation | Normal | ++ | Normal |
| Cold | Normal | - | Normal |
| Hot | Normal | +++ lingering | Normal |
| Electric Pulp Test | Normal | No response | Normal |
| Biting | Normal | +++ | Normal |
| Mobility | Normal | + | Normal |
| Discoloration of Crown | Normal | Discolored, gray | Normal |
| Periodontal Findings | Normal | Normal | Normal |

FIG. 5

SCAFFOLDS, SYSTEMS, METHODS, AND COMPUTER PROGRAM PRODUCTS FOR REGENERATING A PULP

BACKGROUND

Field

Embodiments of the present inventions are generally related to scaffolds for regenerating a pulp in a root canal.

Background

A tooth includes a root canal that encases a pulp. Bacteria introduced into the pulp can cause inflammation or infection. Once the pulp becomes inflamed or infected, the pulp can be removed to restore the area to health. To prevent bacteria from entering the root canal after removing the pulp, inactivate or entomb remaining bacteria, or seal the root canal from infiltration of external tissue fluids emanating from the tooth-supporting structures, the canal is typically obturated using a filler material. The filler material typically includes, for example, gutta percha placed incrementally with lateral compaction of individual gutta percha cones, gutta percha placed incrementally with warm vertical compaction, a single gutta percha cone, gutta percha on a carrier of a similar or different core material, a polymeric hydrogel attached to a central nylon core, or a sealer-only material applied to the full length of the canal.

BRIEF SUMMARY

In some embodiments, a scaffold for regenerating a root canal pulp includes a body having a pre-formed contour that closely matches a contour of the root canal, wherein the body is made of one or more materials that promote the transport of nutrients, oxygen, and waste between the wall of the root canal and the body.

In some embodiments, a method of making a customized regenerative scaffold includes generating a three-dimensional image of a root canal; and manufacturing the regenerative scaffold based on the three-dimensional image of the root canal, the customized regenerative scaffold having a contour that closely matches a contour of the root canal.

In some embodiments, a method of treating pulpal damage includes generating a three-dimensional image of a root canal; manufacturing a customized regenerative scaffold based on the three-dimensional image of the root canal, the customized regenerative scaffold having a preformed contour that closely matches a contour of the root canal; and inserting the customized regenerative scaffold into the root canal.

In some embodiments, a system for generating a customized regenerative scaffold includes a computational device comprising a processor configured to generate a three-dimensional model of a root canal or the regenerative scaffold from a three-dimensional image of the root canal; and a computer controlled manufacturing system configured to manufacture the customized regenerative scaffold using the three-dimensional model.

In some embodiments, a computer implemented method for creating customized regenerative scaffolds includes receiving a 3D image data set representing one or more teeth and displaying, on a user interface, an image of a tooth of the one or more teeth, and receiving at least one user input. The method further includes constructing a 3D output data set from the 3D image data set based on the at least one user input. The 3D output data set is (a) a 3D root canal data set representing the root canal or (b) a 3D regenerative scaffold data set representing a customized regenerative scaffold for the root canal. The method also includes converting the constructed 3D output data set to control data that can be used by a computer controlled manufacturing system to manufacture the customized regenerative scaffold.

In some embodiments, a system includes a memory and one or more processors coupled to the memory. The one or more processors are configured to receive a 3D image data set representing one or more teeth, and display, on a user interface, an image of a tooth of the one or more teeth. The processors are also configured to receive at least one user input, and construct a 3D output data set from the 3D image data set based on the at least one user input. The 3D output data set is (a) a 3D root canal data set representing the root canal or (b) a 3D regenerative scaffold data set representing a customized regenerative scaffold for the root canal. The processors are further configured to convert the constructed 3D output data set to control data that can be used by a computer controlled manufacturing system to manufacture the customized regenerative scaffold.

In some embodiments, a non-transitory computer program product having instructions stored thereon that, when executed by at least one computing device, cause the at least one computing device to perform operations for creating customized regenerative scaffolds. The operations include receiving a 3D image data set representing one or more teeth; displaying, on a user interface, an image of a tooth of the one or more teeth; and receiving at least one user input. The operations further include constructing a 3D output data set from the 3D image data set based on the at least one user input, wherein the 3D output data set is (a) a 3D root canal data set representing the root canal or (b) a 3D regenerative scaffold data set representing a customized regenerative scaffold for the root canal; and converting the constructed 3D output data set to control data that can be used by a computer controlled manufacturing system to manufacture the customized regenerative scaffold.

In some embodiments, a method for creating customized regenerative scaffolds includes receiving a 3D image data set representing one or more teeth; displaying, on a user interface, an image of a tooth of the one or more teeth; and receiving at least one user input. The method also includes constructing a 3D output data set from the 3D image data set based on the at least one user input, wherein the 3D output data set is (a) a 3D root canal data set representing the root canal or (b) a 3D regenerative scaffold data set representing a customized regenerative scaffold for the root canal; and converting the constructed 3D output data set to control data that can be used by a computer controlled manufacturing system to manufacture the customized regenerative scaffold. The method further includes manufacturing the customized regenerative scaffold.

BRIEF DESCRIPTION OF THE DRAWINGS

Embodiments will now be described, by way of example only, with reference to the accompanying schematic drawings in which corresponding reference symbols indicate corresponding parts, and in which:

FIGS. 1A and 1B illustrate (1) a coronal reformation of a human anterior tooth and (2) a cross-sectional reformation of the human anterior tooth of FIG. 1A, respectively. Cross-sectional images are generated perpendicular to the arch-form of the maxilla or mandible.

FIGS. 2A and 2B illustrate (1) a coronal reformation of an abscessed human anterior tooth and (2) a cross-sectional reformation of the human anterior tooth of FIG. 2A, respectively.

FIG. 5 illustrates an exemplary tooth testing matrix.

Figure 3:
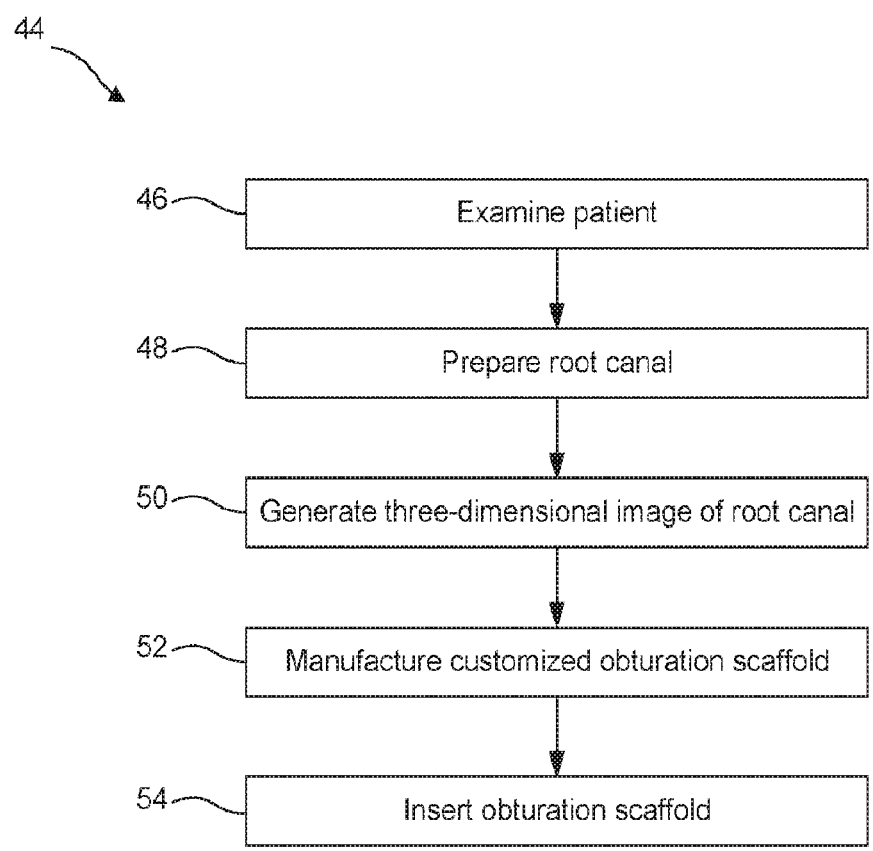
FIG. 3 illustrates a block diagram of a method of treating pulpal damage according to an embodiment.

Features and advantages of the embodiments of the present invention will become more apparent from the detailed description set forth below when taken in conjunction with the drawings.

DETAILED DESCRIPTION

While the invention is described herein with reference to illustrative embodiments for particular applications, it should be understood that the invention is not limited thereto. Those skilled in the art with access to the teachings provided herein will recognize additional modifications, applications, and embodiments within the scope thereof and additional fields in which the invention would be of significant utility.

FIGS. 1A and 1B illustrate a coronal reformation of a human anterior tooth 10 and a cross-sectional reformation of tooth 10, respectively. Tooth 10 includes a root 11 that defines a root canal 12 that contains a pulp 14. Pulp 14 is an unmineralized oral tissue composed of soft connective tissue, vascular, lymphatic and nervous elements. Pulp 14 can extend from a physiologic apex or apical constriction 16, which is usually located about 0.5 mm from a radiographic apex 18, to a pulp horn 20 at a crown 22 of tooth 10. Crown 22 is typically composed of dentin 24 and a layer of enamel 26 that covers a portion of the dentin 24. Root canal 12 can include a coronal portion 28 (the portion nearest crown 22), a middle portion 30, and an apical portion 32 (the portion nearest physiological apex 16), extending from crown 22 to physiological apex 16.

FIGS. 2A and 2B illustrate (1) a coronal reformation of an abscessed human anterior tooth 34 and (2) a cross-sectional reformation of tooth 34, respectively. Sometimes bacteria and/or tissue fluid 36 is introduced into pulp 14 in root canal 12. For example, bacteria and/or tissue fluid 36 can be introduced by caries 38 in tooth 34, periodontal disease, or a fracture. Sometimes bacteria and/or tissue fluid 36 is introduced into a previously root-treated tooth, which can cause inflammation or infection in the surrounding bone, for example, in close approximation to a lateral or accessory canal 40 or to a physiologic terminus 42 of canal 12. Inflammation or infection can cause pain and swelling. Damage to pulp 14 may also occur even if the tooth has no visible deterioration, for example, after a lateral luxation injury. Once pulp 14 becomes inflamed or infected, an endodontic treatment or extraction can be necessary to remove the affected tissue and to restore the area back to health. Once the root canal of a root-treated tooth 12 becomes infected, endodontic revision treatment or extraction can be necessary to remove the affected tissue and to restore the area back to health.

FIG. 3 illustrates a block diagram of a method 44 for treating pulpal damage according to an embodiment. Method 44 includes a patient examination step 46, a root canal preparation step 48, a three-dimensional image generation step 50, a regenerative scaffold manufacturing step 52, and a regenerative scaffold insertion step 54.

In some embodiments, method 44 is performed on a tooth and pulp that are immature (e.g., a tooth of a child). As explained further below, method 44 can regenerate live tissue in the root canal to stimulate regrowth of the pulp and pulp-like tissue and continued development of the root and surrounding tissues. Method 44 can promote biologically-based root maturation, increased thickness of the dentinal walls, and apical closure in teeth with vital pulps, partially vital pulps, and necrotic pulps. In some embodiments, method 44 is performed on a mature tooth and pulp (e.g., a tooth of an adult). For example, instead of filing the root canal of a mature tooth with conventional obturation material, a regenerative scaffold (as explained further below) can be used to regrow the pulp in the mature tooth.

Figure 4:
FIG. 4 is an exemplary periapical radiograph of a maxillary left central incisor.

In some embodiments, at patient diagnostic examination step 46, a dentist, for example, a general dentist or an endodontist, conducts a diagnostic examination of the patient. During the diagnostic examination, the dentist can interview the patient and review the patient medical and dental history. In some embodiments at step 46, the dentist exposes a planar—two-dimensional—radiographic image of the tooth or teeth of interest. FIG. 4 is an exemplary periapical radiographic image of a maxillary left central incisor that could be obtained during the diagnostic examination. The dentist can evaluate the planar radiographic image and then perform a physical examination.

In some embodiments at step 46, the physical examination includes recording responses to various tests including, for example, percussion, palpation, bite stick, thermal, transillumination, and electrical pulp tests. During the physical examination, the dentist can test for signs of pulpal damage, for example, pain on percussion, sensitivity to hot or cold, color changes, soreness, or swelling in the surrounding tissues. These results can be recorded as objective findings in a written matrix such as the one illustrated in FIG. 5. As shown in FIG. 5, the results recorded in the matrix indicate that tooth #9, the maxillary left central incisor, may be infected.

Figure 6:
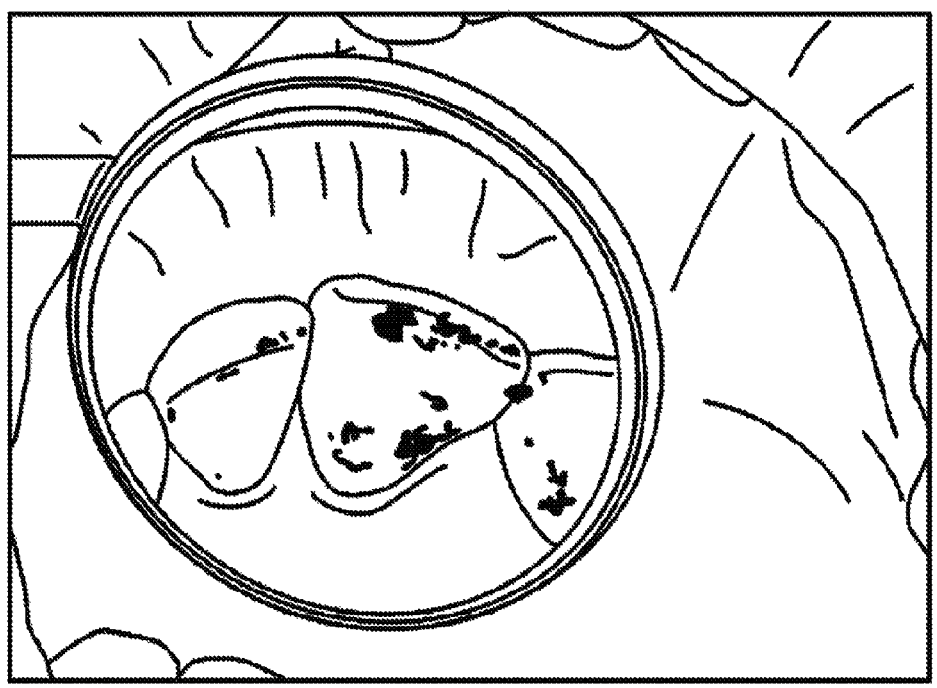
FIG. 6 is a photograph of a central incisor to document the visible light findings and occlusion.

In some embodiments, patient examination step 46 also includes an examination of the tooth or teeth of interest for fracture, for example, by using an explorer, special lighting such as transillumination, staining, and/or using enhanced magnification. In some embodiments, patient examination step 46 also includes an examination of the tooth or teeth of interest for hyper-occlusion. FIG. 6 shows a pre-treatment photographic image that may be exposed to document the examination findings, for example, hyper-occlusion.

Figures 7A, 7B, 7C:
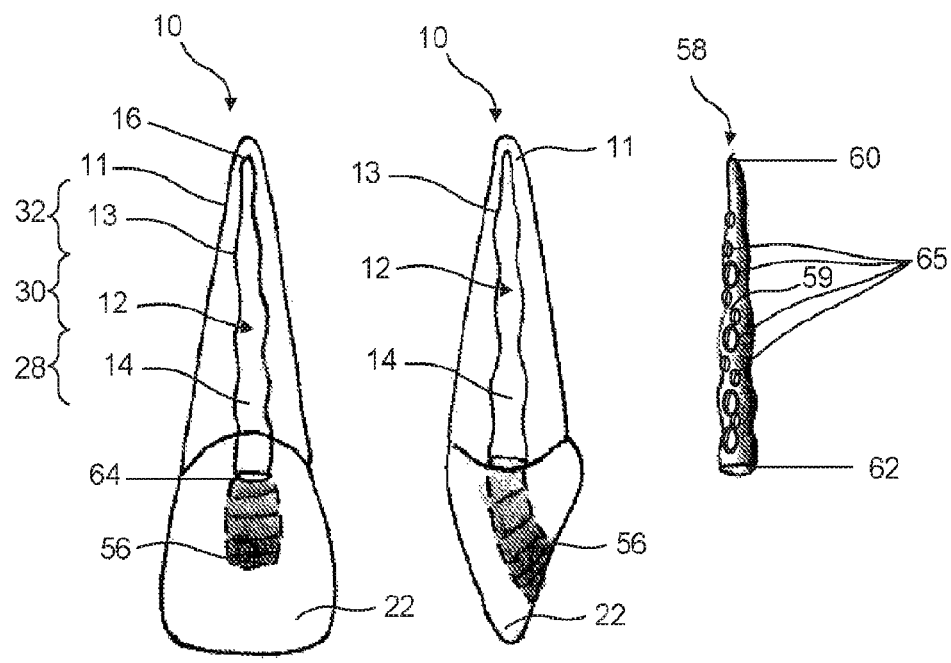
FIGS. 7A, 7B, and 7C illustrate (1) a coronal reformation of a human anterior tooth after irrigation and cleaning and after minimal or no instrumentation; (2) a cross-sectional reformation of the human anterior tooth of FIG. 7A; and (3) a customized regenerative scaffold according to an embodiment, respectively.
Figures 8A, 8B, 8C:
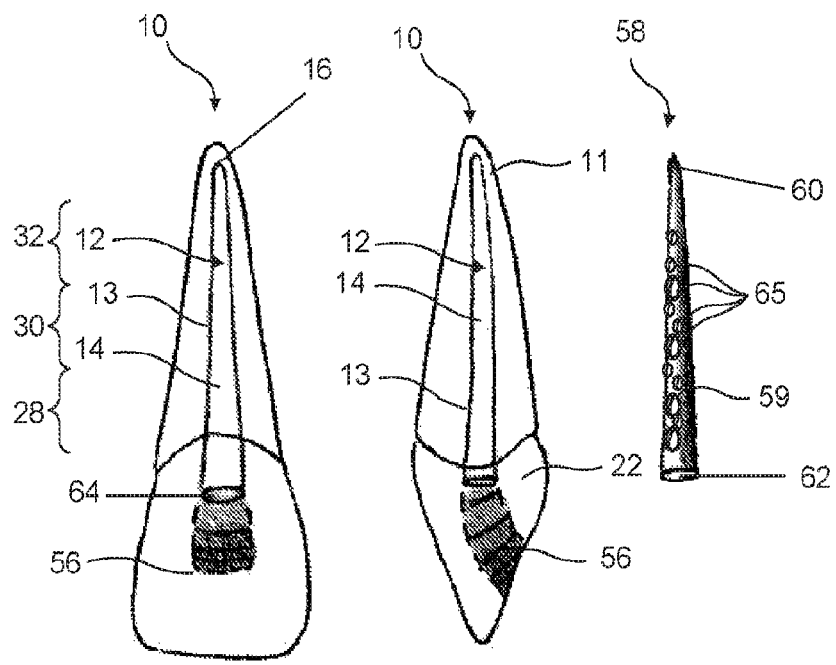
FIGS. 8A, 8B, and 8C illustrate (1) a coronal reformation of a human anterior tooth after irrigation and cleaning and after instrumentation; (2) a cross-sectional reformation of the human anterior tooth of FIG. 8A; and (3) a customized regenerative scaffold according to an embodiment, respectively.

Method 44 can also include a root canal preparation step 48. At step 48, the dentist can prepare root canal 12 of tooth 10. In some embodiments, root canal preparation step 48 includes a routine non-surgical procedure for removing pulp 14 from canal 12, for example, through an access opening 56 (referring to FIGS. 7A, 7B, 8A, and 8B) on an exposed surface of tooth 10 in some embodiments. In some embodiments at step 48, after removing pulp 14, root canal 12 is irrigated and disinfected, for example, by providing an irrigant to remove substantially all traces of tissue, debris, bacteria, and tissue fluid in root canal 12. For example, canal 12 can be irrigated using a needle that delivers the irrigant. In some embodiments at step 48, as shown in FIGS. 7A and 7B, after irrigating and disinfecting, walls 13 (which form the contour of canal 12) of canal 12 are either uninstrumented or lightly instrumented through access opening 56 using, for example, sonic, multisonic or ultrasonic technologies, a laser technique, or any combination thereof. In some embodiments at step 48, as shown in FIGS. 8A and 8B, after irrigating and disinfecting, the walls of canal 12 are moderately or heavily instrumented so that walls 13 of canal 12 form a desired shape. For example, as shown in FIGS. 8A and 8B, walls 13 of canal 12 form a conical shape. In some embodiments, the desired shape of walls 13 of canal 12 is a non-conical shape.

In some embodiments, root canal preparation step 48 includes a revision procedure. That is, root canal 12 is retreated or revised because of continued infection after initial endodontic treatment, which can sometimes occur years later. Revision procedures can be necessary when there was suboptimal prior root canal therapy, complicated canal anatomy, or contamination with oral bacteria and/or tissue fluid through a leaking restoration. In some embodiments in which root canal preparation step 48 is a revision procedure, the previously placed root canal filling material is removed from canal 12, and canal 12 is irrigated and disinfected. In some embodiments in which root canal preparation step 48 is a revision procedure, root canal preparation step 48 is performed using an operating microscope with coaxial lighting along with intraoral radiography.

In some embodiments, root canal preparation step 48 is surgical procedure that includes, for example, surgically removing infected root 11 or apex 16 and the surrounding tissue. This procedure is known as apical micro-surgery or an apicoectomy. A surgical operating microscope with coaxial lighting can be used to enhance visualization during such procedures.

Method 44 can also include a three-dimensional image generation step 50. At step 50, a three-dimensional image that includes, at least in part, canal 12 is generated. In some embodiments, the three-dimensional image is a high-resolution three-dimensional image, for example, an image having a resolution in the range of about 75-125 μm voxel size. In some embodiments, the three-dimensional image has a resolution outside of the range of about 75-125 μm voxel size.

In some embodiments at image generation step 50, one or more three-dimensional images are generated.

Figure 9A:
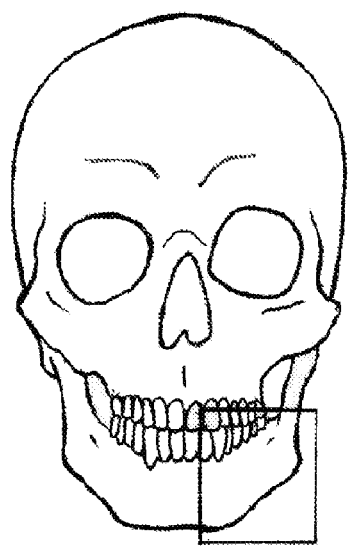
FIGS. 9A, 9B, and 9C illustrate a schematic view of a human skull with, from the left, a limited field of view, a medium field of view, and a large field of view, respectively, according to an embodiment.
Figure 9B:
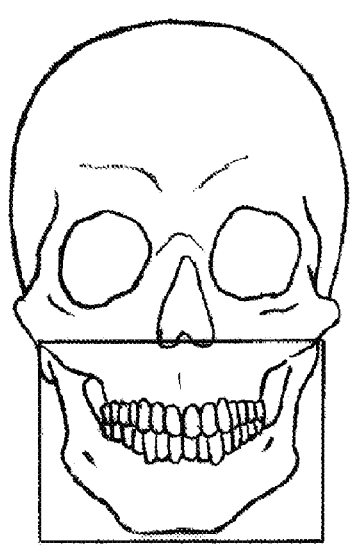
Figure 9C:
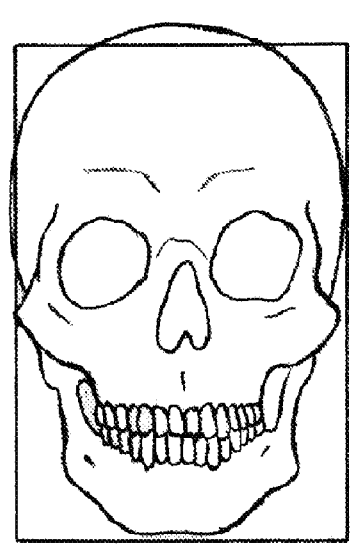
Figure 10A:
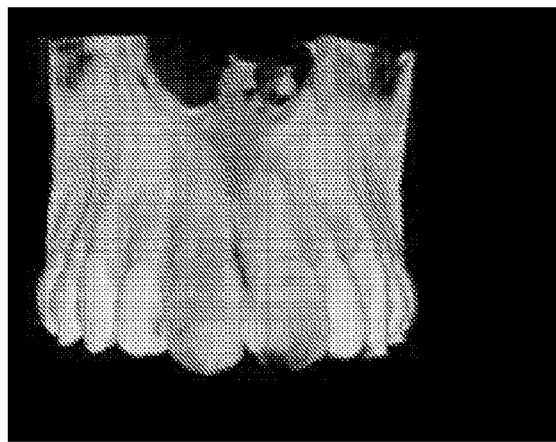
FIGS. 10A-10D illustrate exemplary generated three-dimensional images.
Figure 10B:
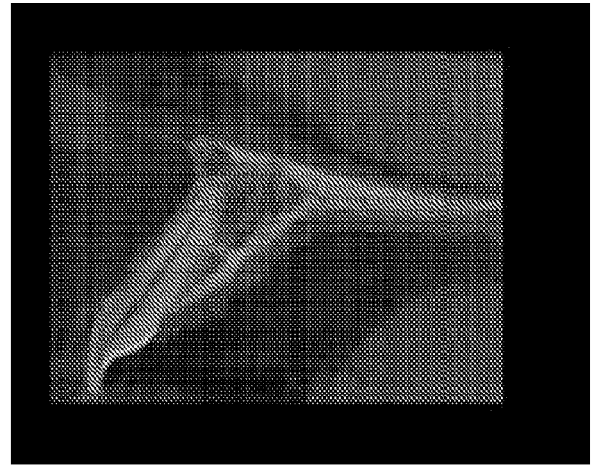
Figure 10C:
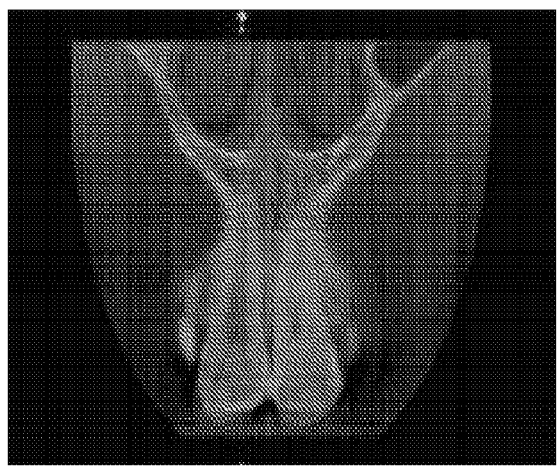
Figure 10D:
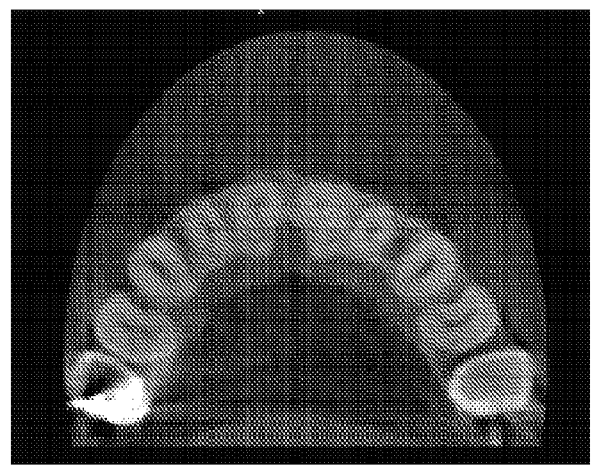

In some embodiments, the three-dimensional image is a tomographic image. In some embodiments, the three-dimensional image is generated by computed tomography (CT), for example, using X-ray CT such as a cone-beam CT (CBCT); magnetic resonance imaging (MM); ultrasound, radiography, optical imaging, or any other suitable three-dimensional imaging technology. The three-dimensional image may have various fields of view (FOV). For example, as shown in FIGS. 9A-9C, the generated three-dimensional image may have a limited FOV as illustrated by the box in FIG. 9A, a medium FOV as illustrated by the box in FIG. 9B, or a large FOV as illustrated by the box in FIG. 9C. FIGS. 10A-10D illustrates exemplary generated three-dimensional images showing a volume-rendered image of the reconstructed surface in FIG. 10A, a cross-sectional reformation in FIG. 10B, a coronal reformation in FIG. 10C, and an axial reformation in FIG. 10D according to an embodiment. The generated three-dimensional image can show a single tooth, a quadrant of teeth, a sextant of teeth, or the entire dentition and surrounding structures in three dimensions in some embodiments.

In some embodiments, the three-dimensional image is generated intra-operatively and post-operatively—concurrently with or after canal preparation step 48. In some embodiments, the three-dimensional image uses special techniques to collimate the scan volume so that it only slightly exceeds the dimensions of the anatomy of interest.

In some embodiments, image generation step 50 is performed at a dentist's office. In some embodiments, step 50 is performed at facility outside of the dentist's office.

Figure 17:
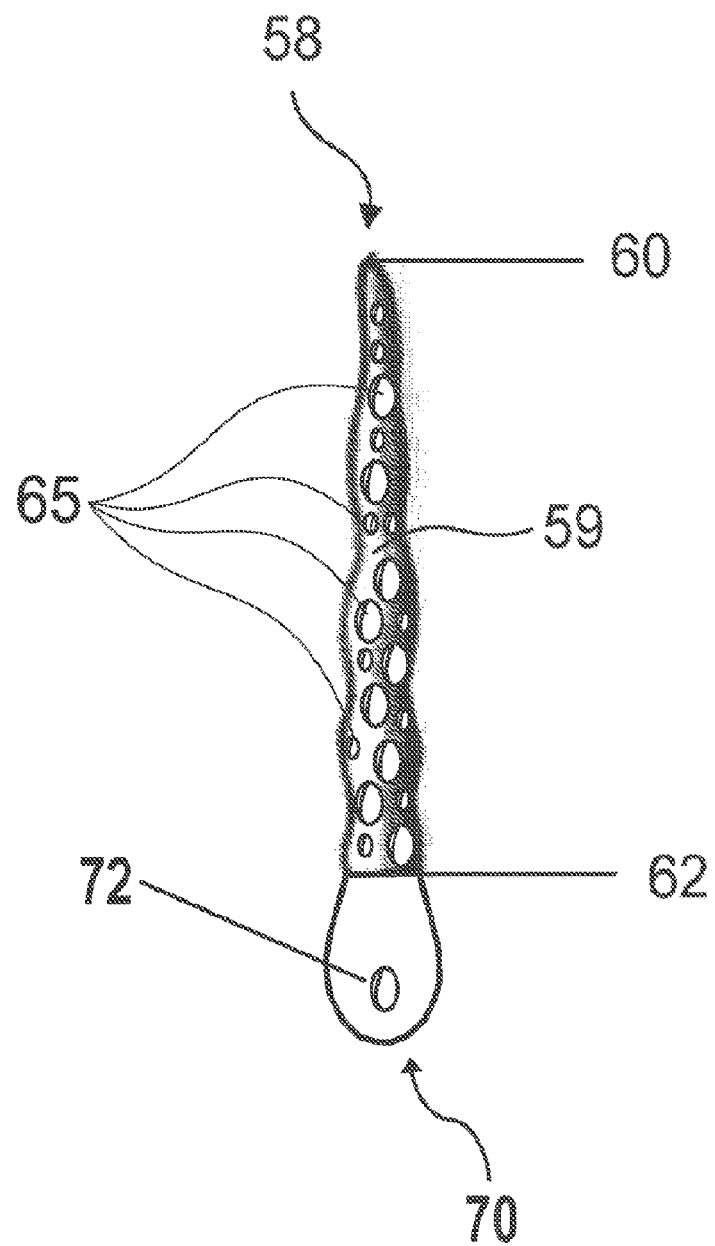
FIG. 17 illustrates a customized regenerative scaffold with a handle and interface, according to an embodiment.

Method 44 can also include a regenerative scaffold manufacturing step 52. At step 52, a customized regenerative scaffold 58 is made. FIGS. 7C, 8C, and 17 illustrate exemplary regenerative scaffolds 58, according to some embodiments. Regenerative scaffold 58 is made of one or more materials and/or is structurally configured to promote the regeneration of a pulp in the root canal. For example, scaffold 58 can include a plurality of openings 65 in some embodiments. In some embodiments, openings 65 can be open or closed pores of the material forming scaffold 58. For example, openings 65 can include closed (filled) material pores, for example, antimicrobial medicaments, antibiotic-eluting materials, macroparticles, and/or nanoparticles. In some embodiments, openings 65 can be intentionally formed spatial gaps or voids. Openings 65 can help promote regeneration of a pulp within root canal 12 and/or structural stability of the regenerating pulp. In some embodiments, regenerative scaffold 58 with openings 65 can be manufactured using a computer controlled manufacturing system, as described further below.

In some embodiments at step 52, a single-piece body 59 of regenerative scaffold 58 is shaped so its preformed contour (i.e., its contour before being inserted into canal 12) closely matches the contour of walls 13 of root canal 12. In some embodiments, the contour of body 59 of scaffold 58 closely matches the contour of walls 13 of root canal 12 such that substantially the entire canal 12 is filled with only scaffold 58 when inserted therein In some embodiments, the gap between any portion of scaffold 58 and walls 13 of root canal 12 is smaller than about 0.5 micrometers. In some embodiments, the contour of body 59 of scaffold 58 closely matches the contour of walls 13 of root canal 12 such that substantially the entire canal 12 is filled with scaffold 58 (and in some embodiments, also a sealant) when inserted therein.

In some embodiments, the contour of body 59 of scaffold 58 is substantially parallel to the contour of root canal 12. In some embodiments, scaffold 58 is made to have an initial volume of about 90 to 110 percent of the volume of root canal 12. In some embodiments, scaffold 58 is about have an initial volume of about 95 to 105 percent of the volume of root canal 12. For example, as shown in FIG. 7C, body 59 of scaffold 58 has a wavy contour that closely matches the wavy contour of walls 13 of canal 12 in FIGS. 7A and 7B. As shown in FIG. 8C, body 59 of scaffold 58 has a substantially conical contour that closely matches the conical contour of walls 13 of canal 12 in FIGS. 8A and 8B. In some embodiments, scaffold 58 has a preformed shape that includes an intermediate portion that has a smaller diameter than proximal and distal portions of scaffold 58, for example, an hour-glass shape.

Figure 16C:
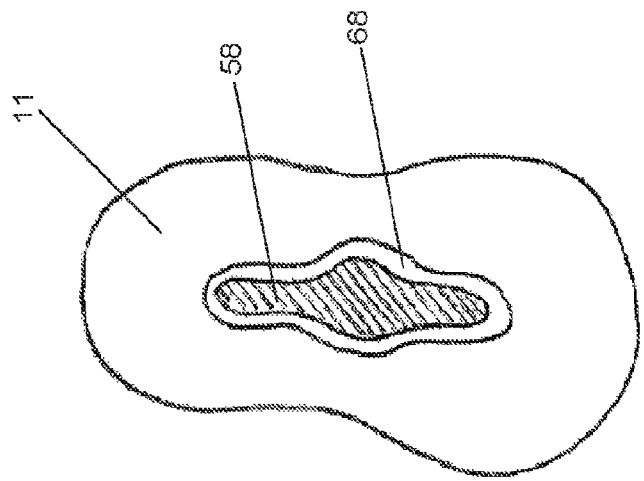
FIGS. 16A, 16B, and 16C illustrate axial reformations of a root and root canal after instrumentation and disinfection with no scaffold, with a non-customized cylindrical scaffold, and a customized regenerative scaffold according to an embodiment, respectively.
Figure 16B:
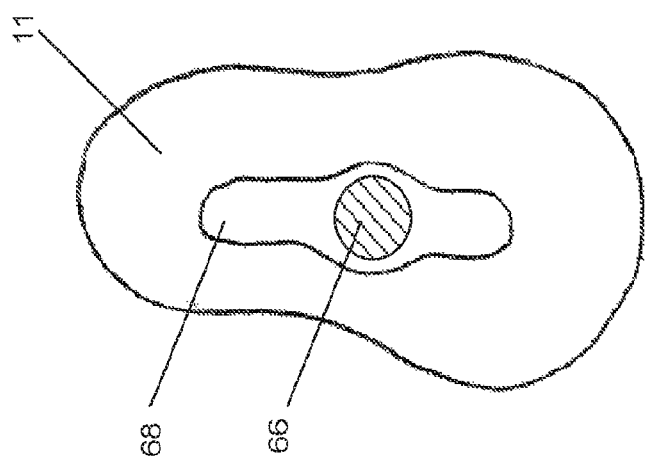
Figure 16A:
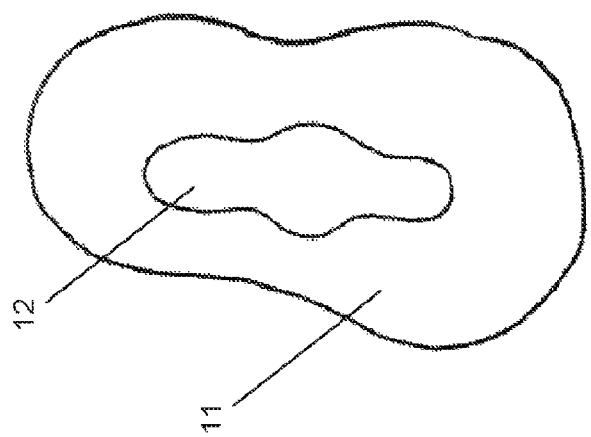

FIGS. 16A, 16B, and 16C illustrate axial reformations of root 11 and root canal 12 (1) with no scaffold 58, (2) with a non-customized cylindrical scaffold, and (3) with customized regenerative scaffold 58 according to an embodiment, respectively, the volume 68 between scaffold 58 and the walls of the root canal is less than volume 68 between the non-customized cylindrical scaffold and the walls of the root canal. Reducing the size volume 68 can promote one or more of cell-biomaterial interactions, cell adhesion, and scaffold deposition.

In some embodiments, as shown in FIGS. 7A, 7C, 8A, and 8C, scaffold 58 has a length such that, when scaffold 58 is inserted in canal 12, an apical end 60 of scaffold 58 is positioned at physiologic apex 16, and a coronal end 62 of scaffold 58 is positioned at the orifice 64 of canal 12. In other embodiments, scaffold 58 has a length such that, when scaffold 58 is inserted in canal 12, apical end 60 is positioned at physiologic apex 16, and coronal end 62 is positioned proximate to access opening 56.

In some embodiments, regenerative scaffold 58 is made of a sterile material. In some embodiments, regenerative scaffold 58 is an inert material. In some embodiments, regenerative scaffold 58 is a biocompatible material. In some embodiments, regenerative scaffold 58 is a sterile, inert, and biocompatible material. In some embodiments, regenerative scaffold 58 is made of a sterile, inert, and/or biocompatible material. In some embodiments, scaffold 58 is made of a material that is antimicrobial to reduce the risk that bacteria will grow in canal 12. For example, scaffold 58 can be made of a material that does not support bacterial growth. In some embodiments, scaffold 58 is made of a material that can be safely applied to avoid overextension into vital anatomic structures. In some embodiments, regenerative scaffold 58 is a biocompatible material that is dimensionally stable. In the context of this application, "dimensionally stable," means that the dimensions and shape of regenerative scaffold 58 remains dimensionally stable after final placement in canal 12. In some embodiments, scaffold 58 is made of a material that is radiopaque.

In some embodiments, regenerative scaffold 58 can be biodegradable or permanent. In some embodiments, regenerative scaffold 58 can be made of one or more natural materials. For example, regenerative scaffold 58 can be made of collagen, gelatin, hyaluronic acid, chitosan, chitosan-based, chitin, tannic acid, polyphenols, or some combination thereof. In some embodiments, regenerative scaffold 58 can be made of one or more synthetic materials. For example, regenerative scaffold 58 can be made of polylactic acid, polyglycolic acid, tricalcium phosphate, hydroxyapatite (HA), polymethylmethacrylate (PMMA), magnesium phosphate, peptide amphiphiles, or some combination thereof. In some embodiments, regenerative scaffold 58 can include mineral trioxide aggregate (MTA) and/or polycaprolactone (PCL). For example, regenerative scaffold 58 can include MTA/PCL to enhance osteogenesis. In some embodiments, regenerative scaffold 58 can include PCL with platelet-rich plasma (PRP). For example, regenerative scaffold 58 can include additively manufactured (e.g., 3D printed) PCL with freeze-dried and/or traditionally prepared PRP. In some embodiments, regenerative scaffold 58 can include biodentine and/or PCL. For example, regenerative scaffold 58 can include 3D printed biodentine/PCL to promote human dental pulp stem cells (HDPSCs) formation. In some embodiments, regenerative scaffold 58 can made of one or more ceramics. For example, regenerative scaffold 58 can made of porous ceramics (e.g., alumina, titania, zirconia oxides, silicon carbide, silica, or some combination thereof). In some embodiments, regenerative scaffold 58 can be made of nanofibers. For example, regenerative scaffold 58 can be made of natural nanofibers or synthetic nanofibers. In some embodiments, regenerative scaffold 58 can made of polydioxanone (PDS), polydimethylsiloxane (PDMS), triple antibiotic paste (TAP) polymers, ciprofloxacin, or some combination thereof.

In some embodiments, regenerative scaffold 58 can be made of antimicrobial medicaments, antibiotic-eluting materials, macroparticles, and/or nanoparticles. In some embodiments, for example, regenerative scaffold 58 can be made of nanoparticles (organic or inorganic) disposed on or in regenerative scaffold 58. For example, nanoparticles can include bioactive glass (BAG) (e.g., silicon oxide(s), sodium oxide(s), calcium oxide(s), potassium oxide(s), or some combination thereof), zinc oxide(s), iron oxide(s), titanium oxide(s), cerium oxide(s), aluminum oxide(s), gold, silver, iron, copper, magnesium, polymer (e.g., alginate, chitosan, or some combination thereof), cadmium sulfide(s), cadmium selenide(s), or some combination thereof. In some embodiments, for example, regenerative scaffold 58 can include chemicals disposed on or in regenerative scaffold 58. For example, chemicals can include macroparticles or antibiotics (e.g., metronidazole, ciprofloxacin, minocycline, or some combination thereof).

In some embodiments, regenerative scaffold 58 can be a customized scaffold. For example, the customized scaffold 58 can be based on a 3D image of root canal 12 in which scaffold 58 is to be inserted. For example, the customized scaffold 58 can be configured to restore root canal 12 to a healthy state. In some embodiments, regenerative scaffold 58 can include a support matrix or openings 65. For example, the support matrix or openings 65 can be configured for cell organization, proliferation, differentiation, vascularization, or some combination thereof, for example, cells can be derived from HDPSCs. In some embodiments, regenerative scaffold 58 can be fabricated by 3D printing. For example, regenerative scaffold 58 can be fabricated by extrusion-based 3D printing in order to control macropore sizes and structures.

In some embodiments, regenerative scaffold 58 can be made of antimicrobial medicaments, antibiotic-eluting materials, and/or nanoparticles suspended in or on regenerative scaffold 58. For example, the regenerative scaffold 58 can be configured to improve the distribution, contact, and/or efficacy of antimicrobial medicaments, antibiotic-eluting materials, or nanoparticles. In some embodiments, regenerative scaffold can include antimicrobial medicaments, antibiotic-eluting materials, and/or nanoparticles in openings 65 of regenerative scaffold 58. For example, openings 65 can form a biocompatible medication delivery system with improved release kinetics for antimicrobial medicaments, antibiotic-eluting materials, and/or nanoparticles.

In some embodiments, regenerative scaffold 58 is either made of or coated with a bioactive and biocompatible material configured to promote dentin remineralization and adhesion to the root canal surface. In some embodiments, the bioactive and biocompatible material can include calcium silicate, for example, tri-calcium silicate or di-calcium silicate. In some embodiments, the material includes nano-synthesized calcium silicates, which can vary in shape and topography which in turn changes the level of bioactivity.

In some embodiments, regenerative scaffold 58 is either made of or coated with a material including a radiopacifier to improve image contrast and visualization of regenerative scaffold 58 in tomographic and planar images generated by, for example, computed tomography (CT) such as cone-beam computed tomography (CBCT), intraoral radiographic imaging, magnetic resonance imaging, or ultrasonic imaging. For example, the radiopacifier can be bismuth oxide (Bi2O3), ytterbium trifluoride (YbF3), or zirconium oxide (ZrO2). In some embodiments, the regenerative scaffold 58 contains nanoparticles of these radiopacifiers.

In some embodiments, regenerative scaffold 58 is a non-dentin color configured to allow a dentist to easily identify regenerative scaffold 58 relative to root canal 12, for example, red, orange, blue, white, or some other dentin contrasting color. In some embodiments, at least a portion of regenerative scaffold 58 is a non-dentin color. For example, coronal end 62 can be a non-dentin color. The non-dentin color allows a dentist to easily identify and distinguish regenerative scaffold 58 from the surrounding tooth structure during, for example, a revision treatment procedure.

In some embodiments, regenerative scaffold 58 comprises an expansive biocompatible material. For example, regenerative scaffold 58 can be made from a material that expands when exposed to a catalyst, for example, moisture or a sealant for cementing scaffold 58 to tooth 10. In such embodiments, regenerative scaffold 58 is manufactured such that upon expansion in situ regenerative scaffold 58 achieves about 100 percent or more than about 100 percent of the volume of root canal 12 such there are essentially no voids between scaffold 58 and the walls of canal 12. In some embodiments, regenerative scaffold 58 is a material that expands when exposed to a catalyst and remains dimensionally stable after expansion. For example, after expansion in situ in canal 12, the dimensions and shape of regenerative scaffold 58 do not shrink. In some embodiments, the expansion ratio of scaffold 58 is constant along the length of scaffold 58. Notably, although the expansion ratio may be constant along the length of scaffold 58, the absolute diametric expansion may vary depending upon the initial preformed diameter of scaffold 58. For example, if scaffold 58 has a 105 percent diametric expansion ratio and the initial shape of scaffold 58 has a 2 mm diameter bottom and a 10 mm diameter top, the bottom diameter will expand 0.1 mm, and the top diameter will expand 0.5 mm. In other embodiments, different longitudinal segments of scaffold 58 can have different expansion ratios. Thus, for example, the coronal segment can be configured to have a higher expansion ratio than the apical segment. Likewise, the coronal segment can be configured to have a higher expansion ratio than the apical segment. Due to the variable dimensions of a patient's root canal, it is understood that the diameter and shape of the regenerative scaffold would vary along its length to match imaged shape of the patient's root canal. It is also understood that an expansive material having different diameters along its length will expand differently.

In some embodiments, regenerative scaffold 58 comprises a non-expansive material.

In some embodiments, regenerative scaffold 58 comprises a material that does not diametrically contract over an extended period of time, for example, a lifetime.

In some embodiments, the density of the material forming regenerative scaffold 58 varies within regenerative scaffold 58. In some embodiments, the density can vary along a width of regenerative scaffold 58. In some embodiments, regenerative scaffold 58 can have a linearly varying density in the radial direction. In some embodiments, regenerative scaffold 58 can have a non-linearly varying density in the radial direction. In some embodiments, the exterior surface at coronal end 62 includes a portion made of a lower density material. In some embodiments, the density can vary along a vertical length of regenerative scaffold 58.

In some embodiments at step 52, regenerative scaffold 58 is manufactured by a system comprising a computational device comprising a processor configured to generate a three-dimensional CAD model of either canal 12 or body 59 of scaffold 58, and a computer controlled manufacturing system. The computational device can be, for example, a computer, a PDA, a tablet, or any other suitable computational device comprising a processor.

The computer controlled manufacturing system can be, for example, a computer numerically controlled machine, an additive manufacturing machine, or any other suitable manufacturing machine. In some embodiments in which the computer controlled manufacturing system is a computer numerically controlled machine, the computer numerically controlled machine can include a lathe, a milling device, or any other subtractive machine. In some embodiments in which the computer controlled manufacturing system is an additive manufacturing machine, the additive manufacturing machine can be a stereolithographic machine, an inkjet printer machine (i.e., a 3D printer), a selective laser sintering machine, a fused deposition modeling machine, or any other suitable additive machine.

In some embodiments, the computer controlled manufacturing system manufactures scaffold 58 using the three-dimensional image obtained at step 50. For example, the three-dimensional image generated at step 50 can be uploaded to the computational device using computer imaging software and stored in memory on the computational device. The computational device can generate a three-dimensional CAD model of canal 12 or of body 59 of scaffold 58 by using the uploaded three-dimensional image. In some embodiments, the three-dimensional CAD model is made by decomposing root canal 12 into cross-sectional layer representations. In some embodiments, the computational device uses the three-dimensional CAD model to generate instructions, for example, numerical files, that drive the computer controlled system to manufacture body 59 of scaffold 58, and then the computational device transmits the instructions to the computer controlled manufacturing system. In some embodiments, the computational device is separate from the computer controlled system. In some embodiments, the computational device is integral with the computer controlled system.

Figure 11:
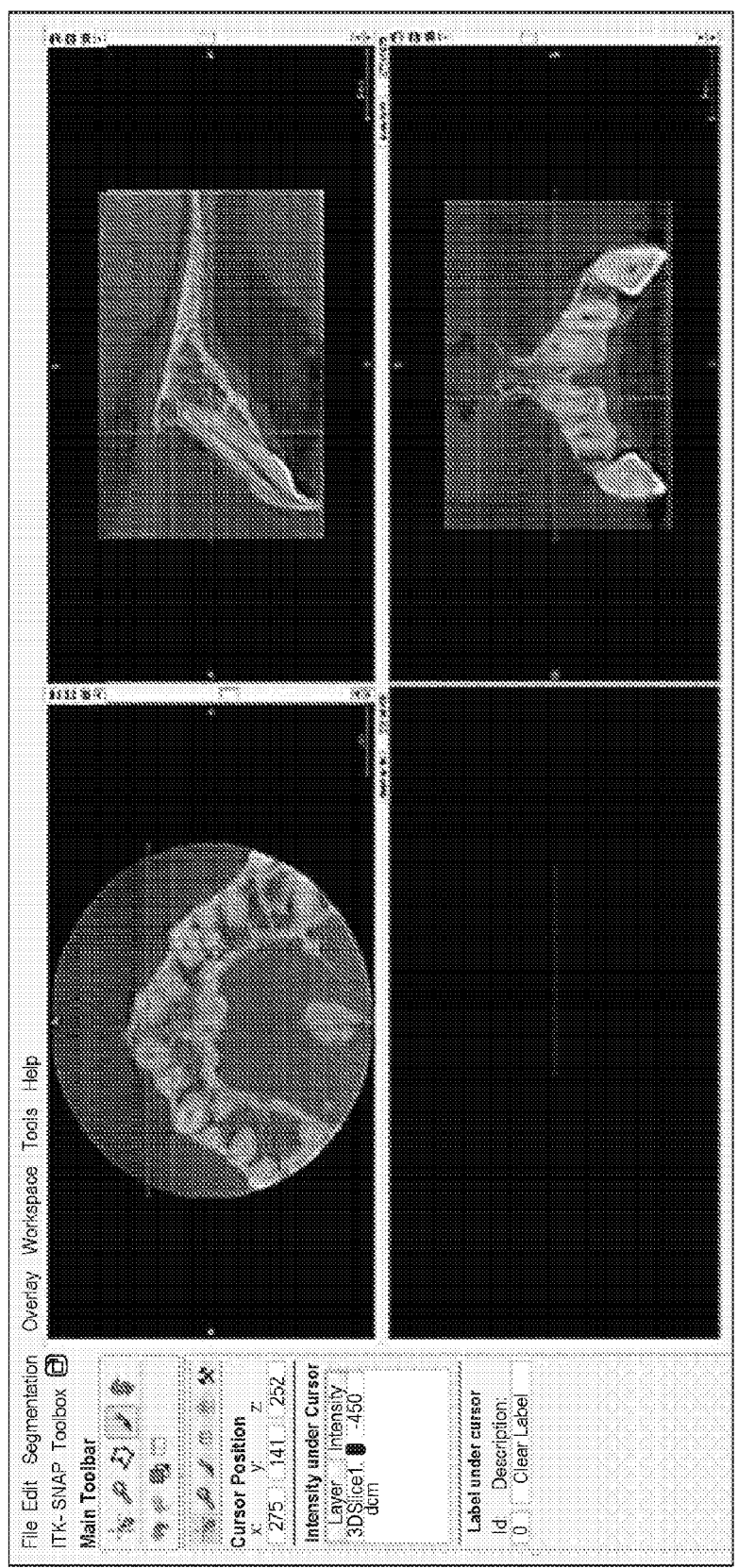
FIGS. 11-15 illustrate exemplary imaging software used to segment a three-dimensional image and to render a volumetric data set of the root canal.
Figure 12:
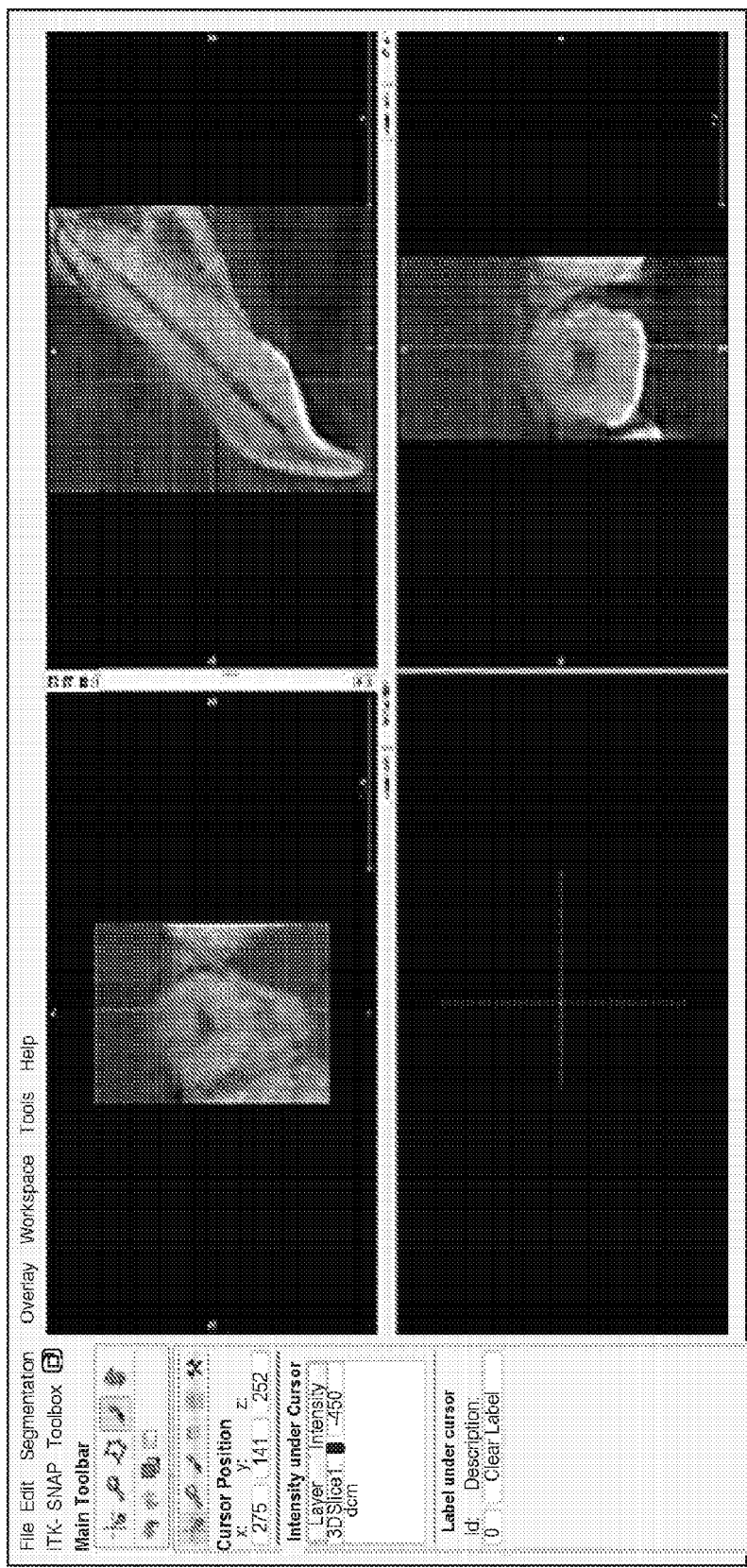
Figure 13:
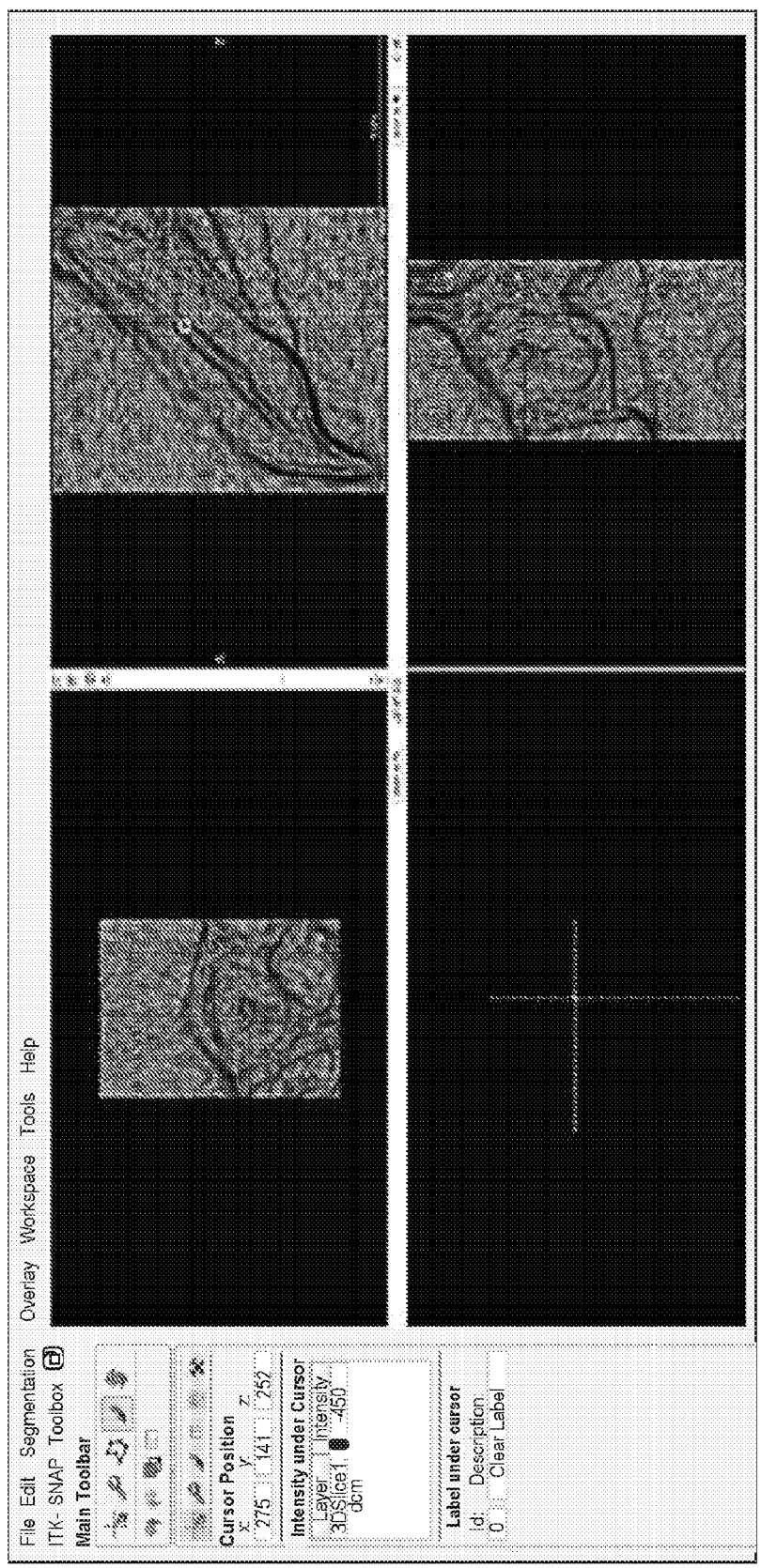

FIGS. 11-15 illustrates exemplary imaging software running on the computational device for generating a three-dimensional CAD model of canal 12 or body 59 of scaffold 58. Particularly, FIG. 11 illustrates a step of uploading the generated three-dimensional image to the computational device. Using the software, a user can identify, for example, by outlining, a region of interest of tooth 10, for example, canal 12, on a graphical user interface on a display of the computational device as illustrated in FIG. 12. Then in some embodiments, the software generates a three-dimensional CAD model of canal 12. For example, FIG. 13 illustrates an exemplary graphical user interface for adjusting the automatic segmentation tool for performing the segmentation iterations with appropriate landmarks applied to generate a three-dimensional CAD model of canal 12 (or scaffold 58). In some embodiments, the software simply and quickly automatically segments root canal 12 and highlights the lateral or accessory canals. In some embodiments, the software uses a patched-based sparse representation and convex optimization.

Figure 14:
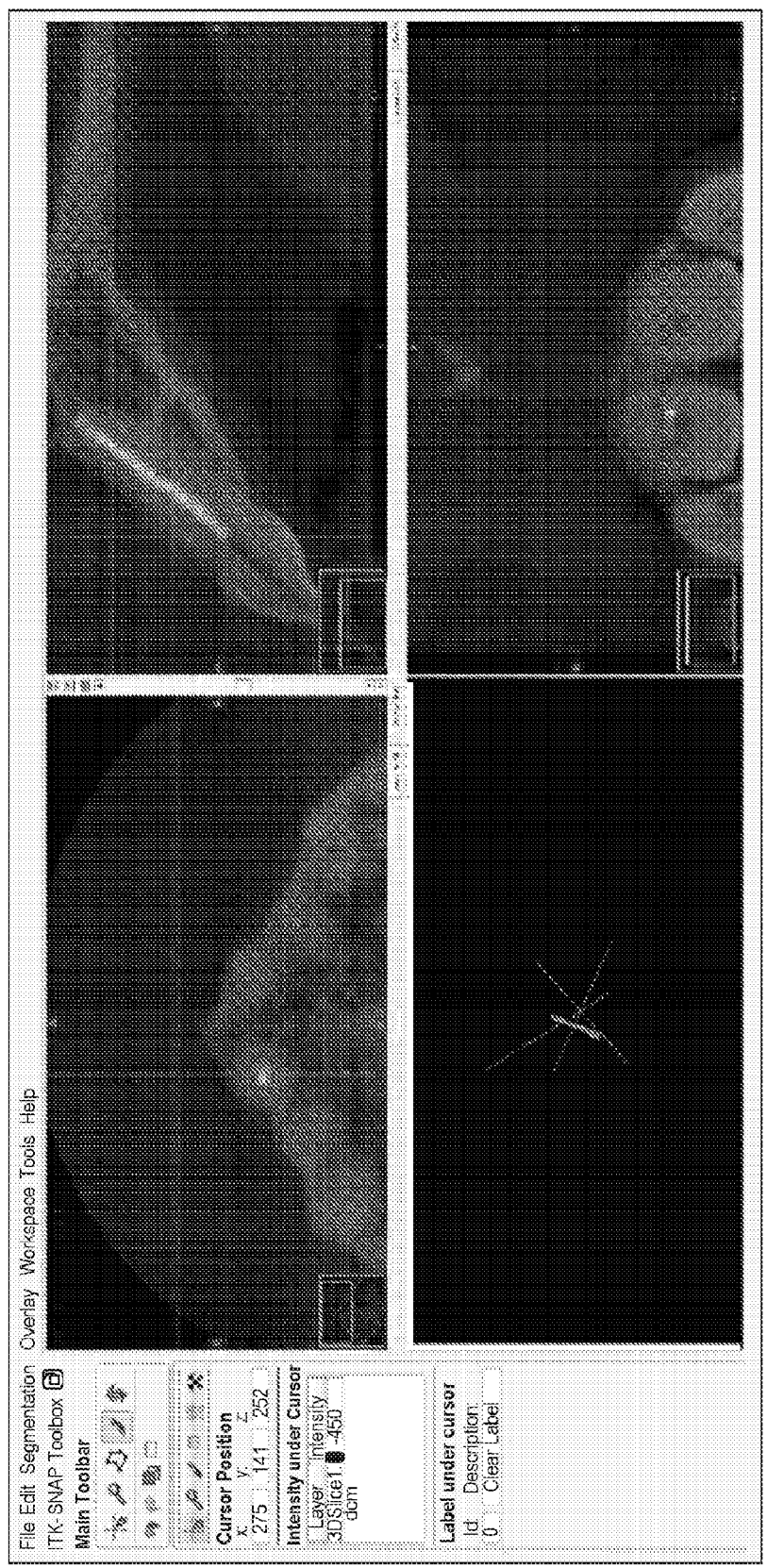
Figure 15:
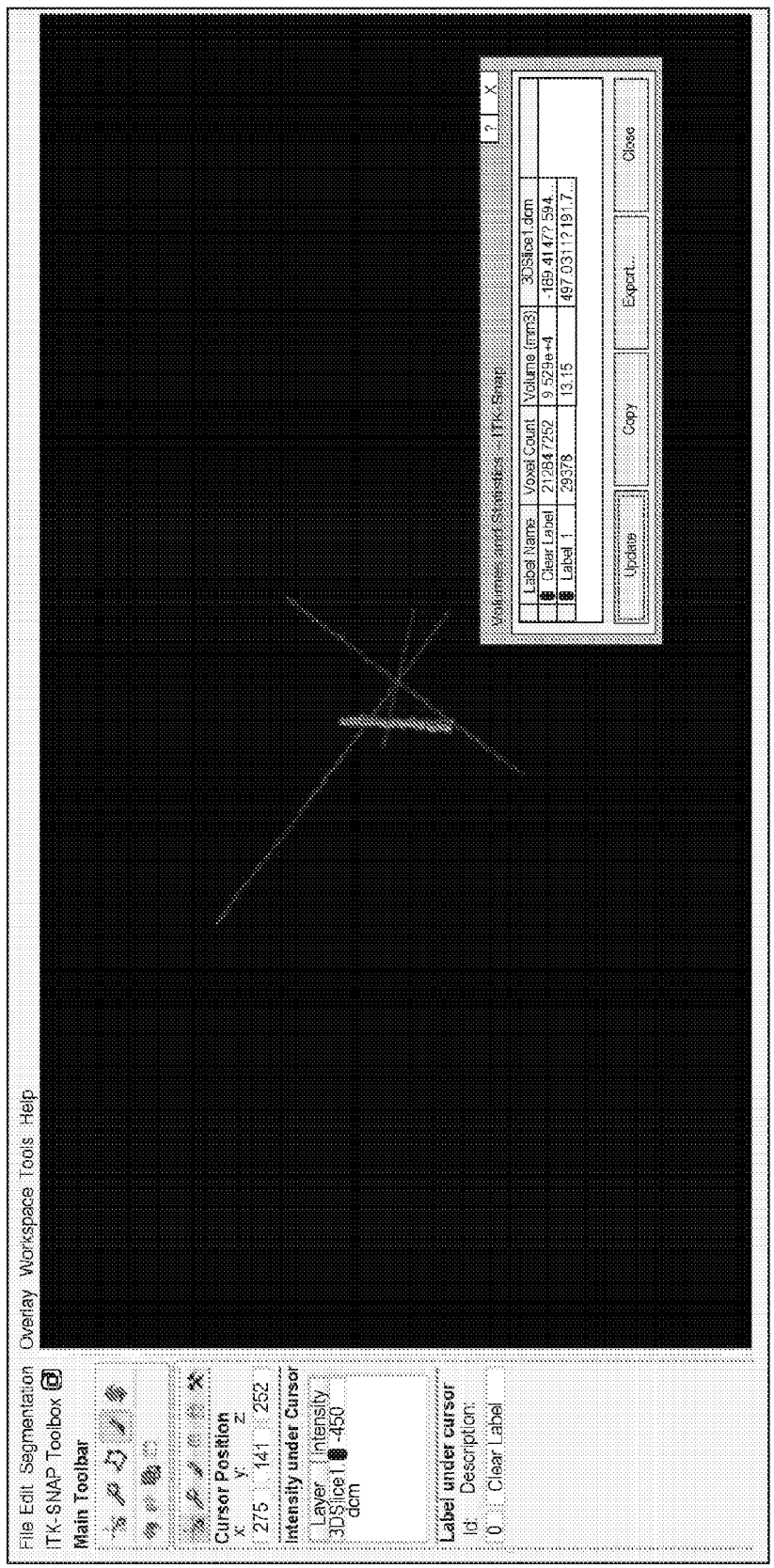

In some embodiments, this CAD model generation substep includes measuring the length and width of canal 12. In some embodiments, the length of canal 12 is measured from physiological apex 16 to access opening 56. In other embodiments, the length of canal 12 is measured from physiological apex 16 to orifice 64 of the canal 12. FIG. 14 illustrates an exemplary graphical user interface for measuring the length and width of canal 12. In some embodiments, the width and length of canal 12 is determined in a slice-by-slice format, for example, by using voxel count and volume. The software then generates a three-dimensional CAD model of canal 12 or body 59 of scaffold 58. FIG. 15 illustrates an exemplary three-dimensional CAD model of body 59 of scaffold 58. From the three-dimensional CAD model, the computational device can generate the file(s) for driving the computer controlled manufacturing system, for example, number files, to make scaffold 58.

In some embodiments, the software superimposes scaffold 58 within canal 12 to allow a user to assess how scaffold 58 fills canal 12, for example, to verify that scaffold 58 fills the entire canal 12 essentially without forming voids.

In some embodiments scaffold generation step 52 occurs at the dentist's office. In some embodiments, scaffold generation step 52 occurs at a facility off-site from dentist's office, and scaffold 58 is shipped to the dentist.

After generating scaffold 58 at step 52, a dentist inserts scaffold 58 within canal 12 at step 54 of method 44. In some embodiments, scaffold 58 is inserted in canal 12 without using a sealant. In some embodiments, scaffold 58 is inserted in canal 12 with a sealant to cement scaffold 58 to tooth 10. In some embodiments in which a sealant is used, canal 12 is coated with sealant before inserting scaffold 58 into canal 12, scaffold 58 is coated with sealant, or both. In some embodiments, when scaffold 58 is inserted into canal 12 with or without using sealant, canal 12 is essentially fully sealed without voids. In some embodiments, a sealant is used to cement scaffold 58 to canal 12. In some embodiments, when inserted, scaffold 58 renders canal 12 substantially impervious to bacterial and tissue fluid infiltration or entombs any remaining bacteria in canal 12.

In some embodiments, step 52 also includes placing a permanent restoration in access opening 56 to seal scaffold 58 within canal 12.

In some embodiments, scaffold 58 can be inserted into canal 12 with minimal force, for example, because the preformed contour of body 59 of scaffold 58 closely matches the contour of canal 12. Accordingly, the risk of tooth fracture can be minimized.

In some embodiments, one or more of steps 46, 48, 50, and 52 are omitted from method 44. For example, step 46 may be omitted.

In some embodiments, regenerative scaffold 58 can include an electrical conducting pathway such that regenerative scaffold 58 can be used in conjunction with an electronic apex locator (EAL) device. In some embodiments, the electrical conducting pathway can extend between apical end 60 and coronal end 62 or the coronal end of a handle 70 (described further below). A portion of the electrical conducting pathway, for example, the portion at coronal end 62, is electrically coupled via a cable to an EAL device that measures, for example, the electrical resistance, impedance, or capacitance to detect physiologic apex 16 of root canal 12. For example, the EAL device can measure the ratio change between capacitance and impedance as regenerative scaffold 58 approaches physiologic apex 16 of root canal 12 to detect when, for example, apical end 60 of regenerative scaffold 58 is at physiologic apex 16 of root canal 12. For example, capacitance increases significantly near physiologic apex 16 of root canal 12, while impedance decreases significantly near physiologic apex 16 of root canal 12. The ratio change in capacitance and impedance can be outputted as an audio signal (e.g., periodic tone) to indicate when regenerative scaffold 58 nears physiologic apex 16 of root canal 12. In such embodiments, regenerative scaffold 58 and the EAL device can be used to ensure regenerative scaffold 58 is fully inserted in root canal 12, instead of or in addition to using tomographic and planar images generated by, for example, computed tomography (CT) such as cone-beam computed tomography (CBCT), intraoral radiographic imaging, magnetic resonance imaging, or ultrasonic imaging.

In some embodiments, the electrical conducting pathway is formed by either an internal or external wire extending from apical end 60 to coronal end 62. For example, the wire can be centered throughout regenerative scaffold 58, or the wire can be disposed on the exterior surface of regenerative scaffold 58. In some embodiments, the entire regenerative scaffold 58 is made of an electrically conductive material such that the entire regenerative scaffold 58 forms the electrical conducting pathway. In some embodiments, the electrically conductive material can be a metal or metal alloy, for example, gold, silver, platinum, aluminum, copper, titanium, titanium gold, nickel-titanium, titanium nitride, indium tin oxide, tin oxide, palladium, and stainless steel. In some embodiments, the electrically conductive material can be a conductive polymer, for example, polyaniline, polypyrrole, doped polyacetylene, polythiophenes, polyazulene, polyfuran, polyisoprene, and any other suitable conductive plastics.

In some embodiments, regenerative scaffold 58 can also include a handle 70 configured to allow a dentist to manipulate regenerative scaffold 58, for example, to allow the dentist to easily move regenerative scaffold 58 relative to root canal 12. FIG. 17 illustrates an exemplary regenerative scaffold 58 with handle 70 according to an embodiment. Handle 70 can be formed at coronal end 62 of regenerative scaffold 58. Handle 70 can have any suitable shape that a dentist can grip using, for example, fingers or an instrument configured to engage handle 70, thereby allowing the dentist to insert, adjust, or remove regenerative scaffold 58 relative to root canal 12. In some embodiments, handle 70 can have an elongated disc shape (as shown in FIG. 17), a prolate spheroid, a three-dimensional polygonal shape (e.g., post, prism, box, cuboid, orthotope, etc.), spheroid shape (e.g., oblate, prolate, etc.), ovoid shape, cylindrical shape, a conical shape, or any other suitable shape. During use, the dentist can grip handle 70 with the dentist's fingers or with an instrument configured to engage handle 70, and then insert, adjust, or remove regenerative scaffold 58 in root canal 12 by manipulating handle 70.

In some embodiments, handle 70 can include an interface 72 that is configured to cooperatively engage with a tool, for example, a probe with a hook, explorer, carver, pliers, wire, excavator, or forceps. In some embodiments, interface 72 can be, for example, a circular through-hole, positioned above an axial centerline of handle 70. Such a circular through-hole interface 72 can be configured to receive a corresponding shaped protrusion (e.g., a hook or prong) of the tool. In other embodiments, interface 72 can be a recess, protrusion (e.g., a post or hook), or groove formed in handle 70 configured to cooperatively engage with a removal tool. During use, the dentist can engage interface 72 with the tool and then insert, adjust, or remove regenerative scaffold 58 in root canal 12 by manipulating the tool.

Figure 18:
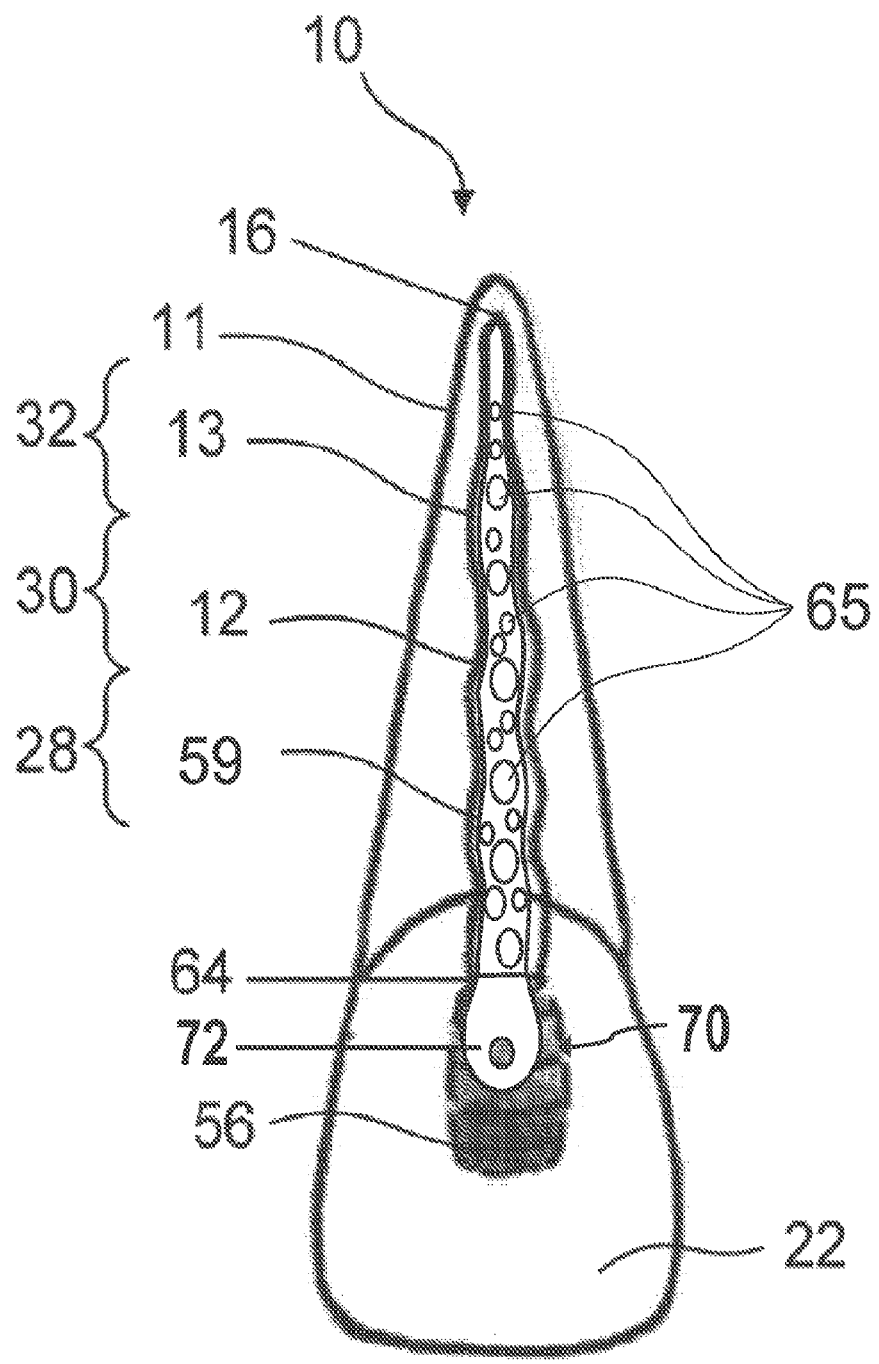
FIG. 18 illustrates a lingual view of a human anterior tooth after irrigation and cleaning and after insertion of a customized regenerative scaffold with a handle and interface, according to an embodiment.

FIG. 18 illustrates a lingual view of human anterior tooth 10 with an exemplary regenerative scaffold 58 with handle 70 inserted within root canal 12. A dentist can remove or adjust regenerative scaffold 58 within root canal 12 by manipulating handle 70, for example, by engaging interface 72 with the tool and then manipulating the tool. After regenerative scaffold 58 is positioned correctly in root canal 12, either handle 70 can be removed from coronal end 62 of regenerative scaffold 58, for example, by cutting handle 70 off using a rotary drill or other tool, or handle 70 can simply be covered by filling material that fills access opening 56 of tooth 10. In some embodiments, handle 70 can be removed at the root canal orifice by applying a reciprocating (i.e., back and forth) rotational force to handle 70. In some embodiments, pre-formed single-piece body 59 includes scoring or a notch at the orifice level that facilitates removal of handle 70. In some embodiments, pre-formed single-piece body 59 has colorized lines or other measurement markings that show the length from the physiologic apex to the orifice. In some embodiments in which handle 70 is not removed, handle 70 can define a smooth surface or be made of a material that does not bond to a sealant or filling material so that regenerative scaffold 58 can be more easily removed from root canal 12. In some embodiments, regenerative scaffold 58 and handle 70 can be sized such that handle 70 is positioned below orifice 64 of root canal 12.

Figure 19:
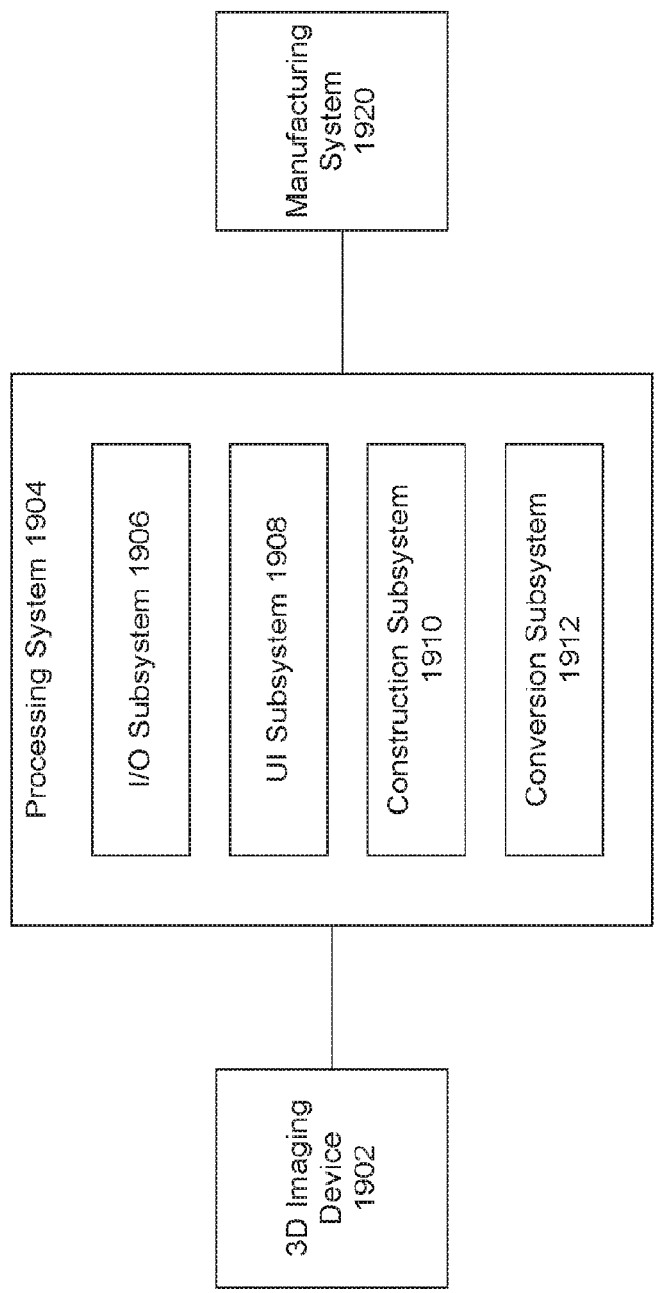
FIG. 19 is a diagram illustrating an example processing system in an environment for creating customized regenerative scaffolds, according to an embodiment.

FIG. 19 is a diagram illustrating an example processing system 1904 in environment 1900 for creating customized regenerative scaffolds according to any one of the above described embodiments. In the embodiment of FIG. 19, processing system 1904 includes four subsystems: I/O (input/output) subsystem 1906, UI (user interface) sub system 1908, construction sub system 1910, and conversion sub system 1912. Each subsystem is described below in turn.

I/O subsystem 1906 receives 3D (three-dimensional) image data sets produced by 3D imaging device 1902. A 3D image data set may represent one or more teeth scanned by 3D imaging device 1902. In some embodiments, 3D imaging device 1902 may transmit the 3D image data set to processing system 1904 via a wired or a wireless connection after 3D imaging device 1902 finishes scanning the patient. A user may also transfer a 3D image data set to processing system 1904 using a storage medium such as a USB flash drive, or an external hard drive, in some embodiments.

UI subsystem 1908 provides user interfaces that allow a user to interact with processing system 1904. For example, UI subsystem 1908 may provide a user interface displaying, for example, on a display, different choices for treatment plan types and prompting the user to make a selection. UI subsystem 1908 may then receive the user selection as one or more user inputs via, for example, a keyboard, mouse, touch-screen, or any other suitable user input device. In another example, UI subsystem 1908 may also display, for example, on the display, a 2D reformation (e.g., a two-dimensional image) of the 3D image data set to the user, and allowing the user to indicate where are the physiologic apex of the root canal, the orifice of the root canal, or both in the 2D reformation of at least one tooth represented in the 3D image data set. UI subsystem 1908 may then receive the user indication of at least one of the physiologic apex and the orifice as another one or more user inputs via, for example, a keyboard, mouse, touch-screen, or any other suitable user input device. In yet another example, UI subsystem 1908 may present a 2D reformation of the 3D image data set to the user and allow the user to indicate areas of pixels, on the display, that form a region representing the root canal of the tooth.

Based on information from the various user inputs, construction subsystem 1910 constructs 3D output data sets from the 3D image data sets. In some embodiments, the 3D output data set may be a 3D root canal data set representing the volume of the root canal. In some embodiments, the 3D output data set may also be a 3D regenerative scaffold data set representing the volume of a customized regenerative scaffold for the root canal.

After construction subsystem 1910 constructs a 3D output data set from a 3D image data set based on the various user inputs, conversion subsystem 1912 may convert the constructed 3D output data set to control data. Computer controlled manufacturing system 1920 may use the control data to manufacture the regenerative scaffold. The manufactured regenerative scaffold can embody the features of any one of the above described embodiments. I/O subsystem 1906 may transmit the control data to manufacturing system 1920 via a wired or wireless connection after conversion subsystem 1912 converts the 3D output data set to the control data. A user may also transfer the control data to manufacturing system 1920 using a storage medium such as a USB flash drive, or an external hard drive, in some embodiments.

Figure 20:
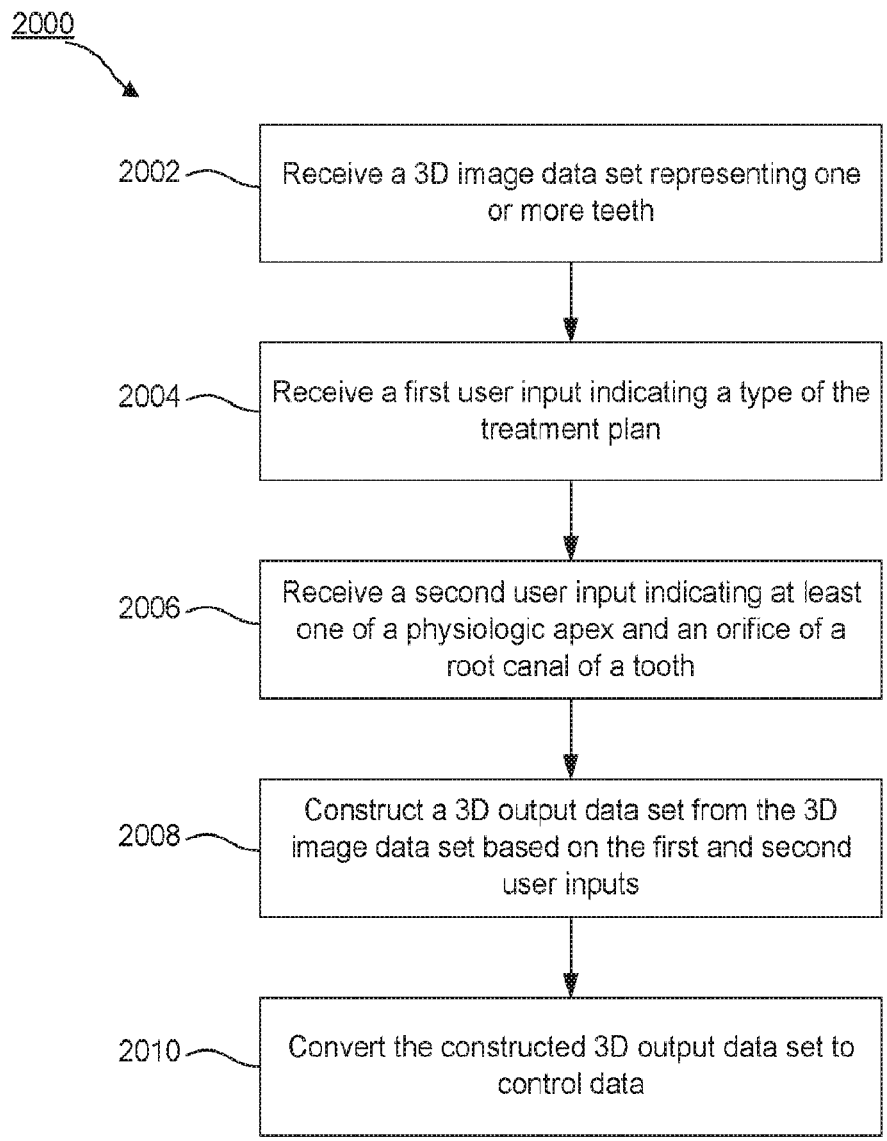
FIG. 20 is a flowchart illustrating a computer implemented method for creating customized regenerative scaffolds, according to an embodiment.

FIG. 20 is a flowchart illustrating computer implemented method 2000 for creating customized regenerative scaffolds, according to an embodiment.

Method 2000 begins at step 2002, where I/O subsystem 1906 receives a 3D image data set. The 3D image data set may represent one or more teeth. The one or more teeth may include an infected tooth to be treated (or a treated tooth). The 3D image data set may be produced by a 3D imaging device, such as 3D imaging device 1902. In some embodiments, the 3D image data set may be generated by computed tomography (CT), for example, using X-ray CT such as a cone-beam CT (CBCT); magnetic resonance imaging (MM); ultrasound, radiography, optical imaging, or any other suitable three-dimensional imaging technology. The 3D image data set may have various fields of view (FOV).

A 3D image data set may comprise a plurality of voxels. A voxel is a unit of graphic information that defines a point (e.g., a cube) in three-dimensional space. A voxel may have values associated with its size, location, color, intensity, etc. In some embodiments, the 3D image data set may comprise voxels with voxel sizes in the range of about 75-125 μm. In some other embodiments, the voxel sizes may be outside of the range of about 75-125 μm.

Depending on the type of the treatment plan, how construction subsystem 1910 constructs the 3D output data set may vary. UI subsystem 1908 may present a user interface displaying different choices for types of the treatment plans. UI subsystem 1908 may receive one or more first user inputs indicating the type of the treatment plan at step 2004.

For example, example treatment plan types can include the following:

A treatment plan type in which no substantial changes in geometry of the root canal will occur after the user selects the type of treatment plan using UI subsystem 1908. Because the treatment would not change the geometry of the root canal, construction subsystem 1910 may use a 3D image data set based, at least in part, on a preoperative scan of the tooth to construct the 3D output data set. Such treatment plans include, for example, cleaning and disinfection using an instrument that contacts the root canal walls and lightly instruments the canal walls while respecting the canal shape or removes a uniform and quantifiable thickness of the canal wall, using advance irrigation technology with or without sonic or ultrasonic energy, or laser disinfection with little or no modification of the canal wall shape and size. The instrumentation and disinfection may uniformly remove the infected and/or non-infected inner dentin layer of the root canal wall(s), which can be quantified and included in the software, e.g., 100-120% of the root canal volume.

A treatment plan type in which changes in the geometry of the root canal will occur, after the user selects the type of treatment plan using UI subsystem 1908, due to instrumentation using known instrumentation metrics. In some embodiments, instrumentation metrics, including for example, an instrument type, size, and/or shape, may be selected, using UI subsystem 1908, from a virtual instrument library stored in a memory of processing system 1904. For example, a user can select that the root canal will be instrumented using a #351.06 taper instrument; a rotary, machine driven, or hand operated instrument; or any combination of these metrics. Construction module 1910 may construct the 3D output data set based, at least in part, on the known instrumentation metrics and the 3D image data set. In some embodiments, after selecting the instrumentation metrics from the virtual instrument library, UI subsystem 1908 may display an image that superimposes a center of an instrument according the selected instrumentation metrics on a center of the root canal. Using instruments of varying taper can also be selected from the instrument library and superimposed.

A treatment plan type in which changes in the geometry of the root canal will occur, after the user selects the type of treatment plan using UI subsystem 1908, due to instrumentation without using known instrumentation metrics. When instrumentation changes the geometry of the root canal, construction subsystem 1910 may use a 3D image data set based, at least in part, on an intraoperative scan (i.e., after instrumentation) to construct the 3D output data set. For example, the post-instrumentation scan provides a three-dimensional data set that shows all changes to the geometric shape and size of the canal. In some embodiments, this post-instrumentation, three-dimensional scan can be collimated based on the earlier three-dimensional scan so that the scan volume only slightly exceeds the dimensions of the anatomy of interest. In some embodiments, this post-instrumentation, three-dimensional scan would use a positioning jig, laser, or other marking techniques to guide the three-dimensional imaging device to reduce radiation. In some embodiments, this second scan could use a 180-degree rotation scheme instead of a 360 degree rotation scheme to further reduce radiation exposure.

Figure 21:
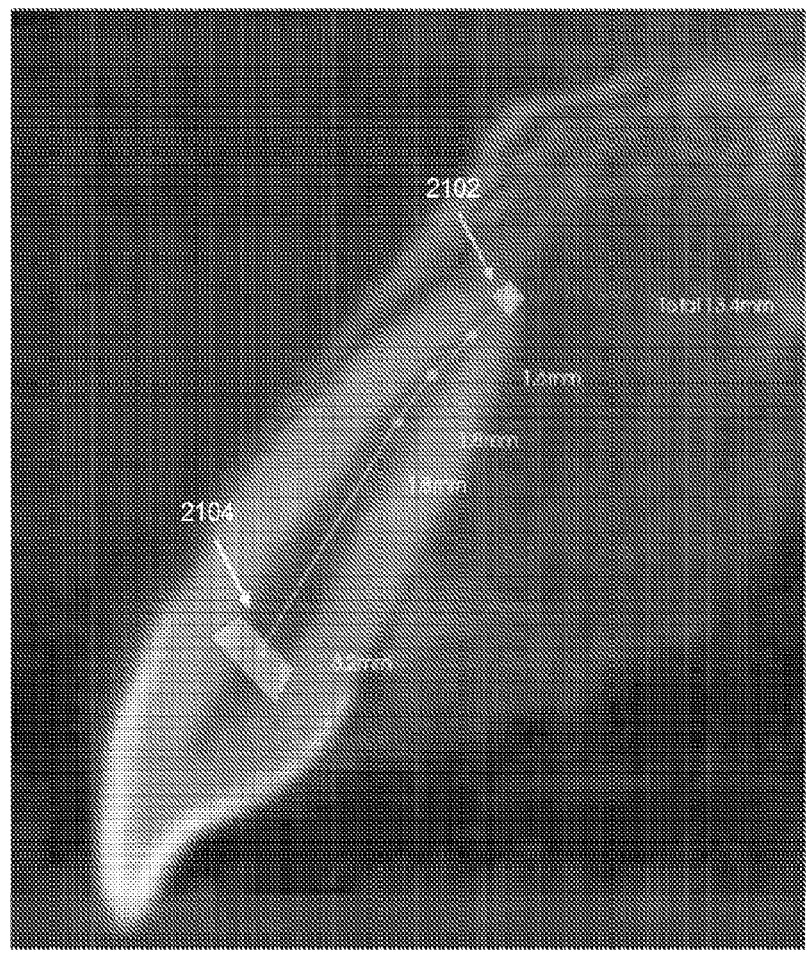
FIG. 21 illustrates an exemplary cross-sectional reformation of a 3D image data set, according to an embodiment.

UI system 1908 may present a 2D reformation of the 3D image data set to the user, for example, by displaying the 2D reformation on a display. At step 2006, UI subsystem 1908 may receive one or more second user inputs indicating the location of at least one of the following: the physiologic apex of the root canal of the tooth and the orifice of the root canal of the tooth. For example, UI subsystem 1908 may present a cross-sectional reformation of the 3D image data set, such as the one shown in FIG. 21, to the user. In some embodiments, the user may use a polyline tool to determine at least one of the physiologic apex and the orifice of the root canal. In some embodiments, the constructed 3D output data set may be bounded by at least one of the physiologic apex and the orifice of the root canal of the tooth as indicated by the one or more second user inputs received at step 2006.

At step 2008, construction subsystem 1910 constructs a 3D output data set from the received 3D image data set. In some embodiments, construction subsystem 1910 may construct the 3D output data set based on the one or more first user inputs (at step 2004) and/or the one or more second user inputs (at step 2006) received by UI subsystem 1908. In one embodiment, the 3D output data set may be a 3D root canal data set representing the volume of the root canal. In another embodiment, the 3D output data set may be a 3D regenerative scaffold data set representing the volume of the customized regenerative scaffold for the root canal.

At step 2010, conversion subsystem 1912 converts the constructed 3D output data set to control data. A computer controlled manufacturing system can use the control data to manufacture the customized regenerative scaffold. The computer controlled manufacturing system can be, for example, a computer numerically controlled machine, an additive manufacturing machine, or any other suitable manufacturing machine. In some embodiments in which the computer controlled manufacturing system is a computer numerically controlled machine, the computer numerically controlled machine can include a lathe, a milling device, or any other subtractive machine. In some embodiments in which the computer controlled manufacturing system is an additive manufacturing machine, the additive manufacturing machine can be a stereolithographic machine, an inkjet printer machine (i.e., a 3D printer), a selective laser sintering machine, a fused deposition modeling machine, or any other suitable additive machine.

For example, conversion subsystem 1912 may convert the constructed 3D output data set to control data in the STL file format. STL (STereoLithography) is a file format native to the stereolithography CAD software created by 3D Systems. The STL file format is a commonly used file format for 3D printing. When used in conjunction with a 3D slicer, it allows a computer to communicate with 3D printer hardware.

Figure 22:
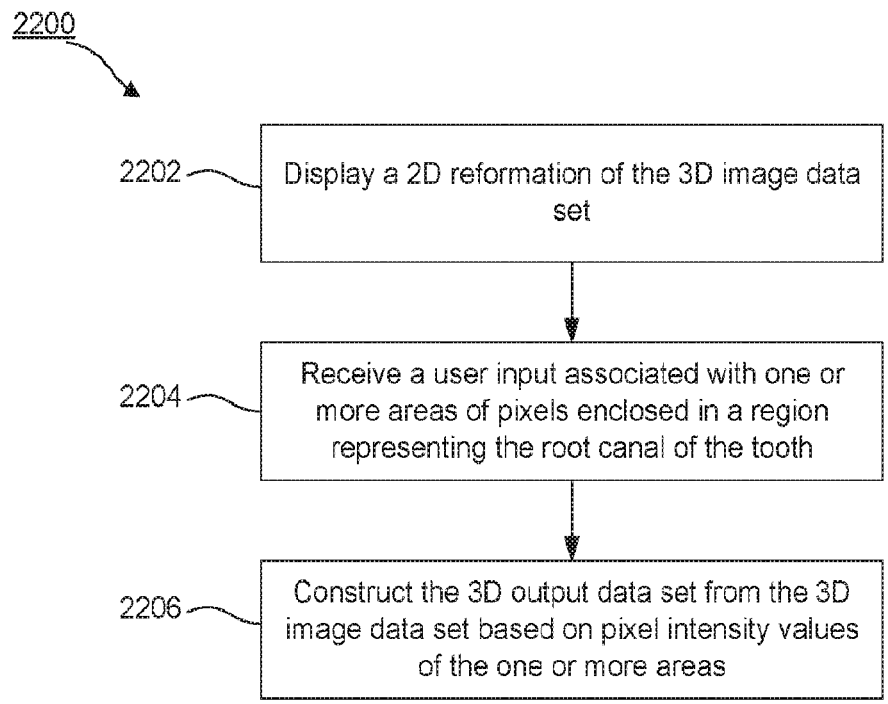
FIG. 22 is a flowchart illustrating a method for constructing a 3D output data set for a treatment with little or no changes in root canal geometry, according to an embodiment.

As described above, how construction subsystem 1910 constructs the 3D output data set may vary, depending on the type of the treatment plan. FIG. 22 is a flowchart illustrating method 2200 for constructing a 3D output data set for a treatment plan type with little or no changes in root canal geometry after the one or more first user inputs (at step 2004) are received by UI subsystem 1908. Method 2200 may construct a 3D output data set based on a 3D image data set from a preoperative scan for a treatment in which the root canal geometry should not change. Because the treatment would not change the geometry of the root canal, construction subsystem 1910 may use the 3D image data set based on a preoperative scan of the tooth to construct the 3D output data set.

For example, method 2200 starts at step 2202, where UI subsystem 1908 displays a 2D reformation of the 3D image data set on a user interface. The 2D reformation comprises a reformatted image of the root canal of the tooth to be treated. For instance, the 2D reformation may be at least one of an orthogonal or oblique multiplanar reformatted image. Examples of 2D cross-sectional reformations include a sagittal reformation, a coronal reformation, and an axial reformation of the root canal of the tooth. A 2D reformation may also be any slice showing a multiplanar reformation. From the 2D reformation, the user may identify a region representing the root canal of the tooth. Within the identified region, the user may mark one or more areas on the 2D reformation. In some embodiments, once volumetric images are generated, and in addition to multiplanar reformation, oblique reformations can be generated that allow the user to slice through the field of view at any angle. For example, the user may mark one or more areas with geometric shapes (such as circles) that represent the root canal of the tooth. Each marked area has a group of pixels inside the area.

To help the user to mark large enough areas inside the displayed root canal in the 2D reformation, UI subsystem 1908 may allow the user to adjust the angle of the long axis of the displayed root canal such that the displayed region representing the root canal is maximized (i.e., larger than other displayed regions representing the root canal at the other angles) in one embodiment. In another embodiment, UI subsystem 1908 may automatically adjust the angle of the long axis of the displayed root canal to an angle such that the displayed region representing the root canal is maximized.

At step 2204, after the user completes the marking at step 2202, UI subsystem 1908 receives one or more user inputs associated with one or more areas representing the root canal, as displayed in the 2D reformation.

At step 2206, construction subsystem 1910 constructs the 3D output data set from the 3D image data set based on at least one of pixel intensity values, Gaussian blurring values, and non-Gaussian blurring values of the one or more marked areas from step 2204. For example, construction subsystem 1910 may construct the 3D output data set from the 3D image data set using thresholding of at least one of pixel intensity values, Gaussian blurring values, and non-Gaussian blurring values of the one or more marked areas from step 2204, in some embodiments. In some embodiments, other segmentation technologies may be used in the segmentation process, namely edge detection and region growing technologies. Construction subsystem 1910 may use manual or automatic segmentation techniques to construct the 3D output data set from the 3D image data set based on at least one of pixel intensity values, Gaussian blurring values, and non-Gaussian blurring values of the one or more areas. For example, construction subsystem 1910 may create an intensity value range based on the pixel intensity values of the one or more marked areas in the displayed 2D reformation.

In one embodiment, construction subsystem 1910 may examine all of pixels in the marked one or more areas to determine a minimum pixel intensity value ("Minimum") and a maximum pixel intensity value ("Maximum") of the one or more marked areas. Construction subsystem 1910 may use the determined minimum and maximum pixel intensity values as the lower and upper bounds of the intensity value range, respectively. In other words, the intensity value range may be [Minimum, Maximum]. The determined minimum and maximum pixel intensity values may not cover all the intensity values of voxels, that represents the root canal of the tooth, of the 3D image data set. So, the intensity value range may be "stretched" by a stretch factor. For example, the intensity value range may be [1.1*Minimum, 1.1*Maximum] (1.1 being the stretch factor).

In other embodiments, construction subsystem 1910 may calculate an average pixel intensity value ("Average") of the one or more marked areas. Construction subsystem 1910 may also calculate a standard deviation value ("StdDev") of pixel intensity values in the one or more marked areas. Construction subsystem 1910 may create the intensity value range based on the average pixel intensity value and the standard deviation value. For example, in one embodiment, the intensity value range may be [Average−StdDev, Average+StdDev]. A multiple or a fraction of the standard deviation value may be used. For example, in another embodiment, the intensity value range may be [Average−2*StdDev, Average+2*StdDev]. In yet another embodiment, the intensity value range may be [Average−0.5*StdDev, Average+0.5*StdDev]. In these embodiments, construction subsystem 1910 may use a median (or a mode) pixel intensity value ("Median" or "Mode") of the one or more marked areas, instead of an average pixel intensity value. For example, the intensity value range may be [Median−StdDev, Median+StdDev].

In some embodiments, construction subsystem 1910 may determine a minimum, a maximum, and a standard deviation value of the pixel intensity values of the one or more marked areas from step 2204. Construction subsystem 1910 may then create the intensity value range based on the minimum pixel intensity value, the maximum pixel intensity value, and the standard deviation value. For example, in one embodiment, the intensity value range may be [Minimum−StdDev, Maximum+StdDev]. Again, a multiple or a fraction of the standard deviation value may be be used. In one example, the intensity value range may be [Minimum−2*StdDev, Maximum+2*StdDev]. In another example, the intensity value range may be [Minimum−0.5*StdDev, Maximum+0.5*StdDev].

As described above, a 3D image data set comprises a group of voxels. For each voxel in the 3D image data set, construction subsystem 1910 may determine whether an intensity value associated with the voxel is within the created intensity value range. For a voxel in the group of voxels in the 3D image data set, if the intensity value associated with the voxel is within the created intensity value range, construction subsystem 1910 includes the voxel in the 3D output data set as a voxel representing a volumetric unit (e.g., a cube) inside the root canal. After examining the 3D image data set, the sum of the voxels included in the 3D output data set by construction subsystem 1910 becomes the 3D output data set.

As explained above, method 2200 may construct a 3D output data set for a treatment plan type in which no changes in root canal geometry will occur. But in some embodiments, method 2200 may construct a 3D output data set for a treatment plan in which changes in geometry of the root canal will occur due to instrumentation without using known instrumentation metrics. In such embodiments, construction subsystem 1910 processes a 3D image data set from a post-instrumentation scan, and utilizes method 2200 as described above.

Figure 23:
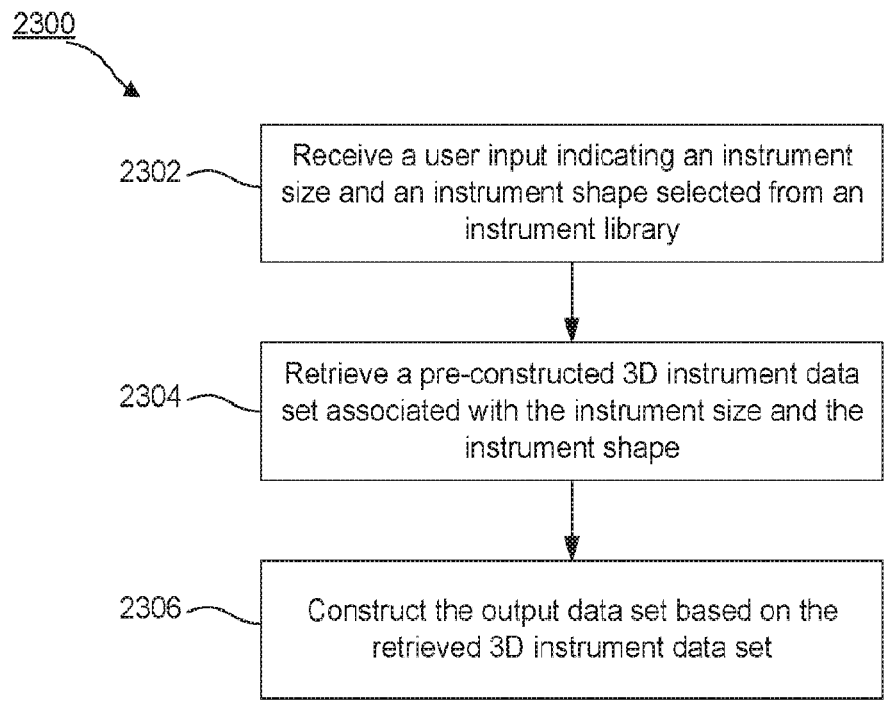
FIG. 23 is a flowchart illustrating a method for constructing a 3D output data set for a treatment plan in which changes in geometry of the root canal will occur due to instrumentation using known instrumentation metrics, according to an embodiment.

FIG. 23 is a flowchart illustrating method 2300 for constructing a 3D output data set for a treatment plan in which changes in geometry of the root canal will occur due to instrumentation using known instrumentation metrics. Method 2300 starts at step 2302, where UI subsystem 1908 receives one or more user inputs indicating known instrumentation metrics (e.g., an instrument type, size, and/or shape) that the user selects from an instrument library, for example, stored in a memory of processing system 1904 and displayed using UI subsystem 1908. (In some embodiments (not shown), the instrumentation metrics are inputted manually using a user input device.) At step 2304, construction subsystem 1910 retrieves a pre-constructed 3D instrument data set associated with the user selected instrumentation metrics. The pre-constructed 3D instrument data set represents the volume of the instrument, in some embodiments. Based on the retrieved 3D instrument data set, construction subsystem 1910 construct the 3D output data set from the 3D image data set at step 2306.

In some embodiments, at step 2306, construction subsystem 1910 extracts a 3D root canal data set from the 3D image data set, using techniques such as the one described in method 2200 to construct the 3D output data set. The 3D root canal data set represents a volume of the preoperative root canal of the tooth. Construction subsystem 1910 may utilize both the 3D root canal data set and the retrieved 3D instrument data set to construct the 3D output data set. The instrument with known instrumentation metrics may change the geometry of the root canal in a known manner. Also the root canal may have surfaces that the instrument may not contact or reach. So in some embodiments, construction subsystem 1910 superimposes the 3D root canal data set and the 3D instrument data set so that the larger shape/diameter of the 3D root canal data set and the 3D instrument data set controls the final shape for the 3D output data set. For example, when the 3D root canal data set and the retrieved 3D instrument data set are represented by different groups of voxels, construction subsystem 1910 may combine voxels of 3D root canal data set and voxels of the retrieved 3D instrument data set to create the 3D output data set.

In some embodiments, the constructed 3D output data set may be bounded by at least one of a physiologic apex and an orifice as indicated by user input. For example, UI subsystem 1908 may allow the user to specify the physiologic apex and the orifice, for example, as two planes, such as planes 2102 and 2104 in FIG. 21, respectively. Construction subsystem 1910 may trim the 3D image data set by excluding voxels outside the two planes in some embodiments. Construction subsystem 1910 may then construct the 3D output data set from the trimmed 3D image data set, using techniques such as the ones described with respect to methods 2200 and 2300. In another embodiment, construction subsystem 1910 may construct the 3D output data set first, and then trim the 3D output data set by excluding voxels outside the two planes 2102 and 2104 before conversion subsystem 1912 converts the final 3D output data set to control data.

In some embodiments, the constructed 3D output data set may be a 3D regenerative scaffold data set representing a volume of a customized regenerative scaffold for the root canal. In these embodiments, construction subsystem 1910 may first construct a 3D root canal data set representing the root canal according to methods 2000, 2200, and 2300. Construction subsystem 1910 then constructs the 3D regenerative scaffold data set based on the 3D root canal data set. Construction subsystem 1910 may trim off (e.g., remove) one or more outer layers of the voxels of the 3D root canal data set to construct the 3D regenerative scaffold data set. Conversion subsystem 1912 uses the 3D regenerative scaffold data set as the 3D output data set and converts the 3D output data set to control data. A computer controlled manufacturing system can use the control data to manufacture the customized regenerative scaffold. Construction subsystem 1910 may determine the number of outer layers of voxels of the 3D root canal data set for removal, such that when the customized regenerative scaffold is inserted in the apical portion of the root canal any voids—between the customized regenerative scaffold and a wall of the root canal—are smaller than a predetermined threshold value. In one embodiment, the threshold value is 2.0 micrometers. In another embodiment, the threshold value is 0.5 micrometers. In some embodiments, the threshold value is more than 2.0 micrometers.

In other embodiments, the 3D output data set constructed according to methods 2000, 2200, and 2300 may be a 3D root canal data set representing the root canal. In these embodiments, conversion subsystem uses the 3D root canal data set as the 3D output data set and converts the 3D output data set to control data. A computer controlled manufacturing system uses the control data to manufacture the customized regenerative scaffold, such that when the customized regenerative scaffold is inserted in the apical portion of the root any voids—between the customized regenerative scaffold and a wall of the root canal—are smaller than a predetermined threshold value. In one embodiment, the threshold value is 2.0 micrometers. In another embodiment, the threshold value is 0.5 micrometers. In some embodiments, the threshold value is more than 2.0 micrometers.

Figure 24:
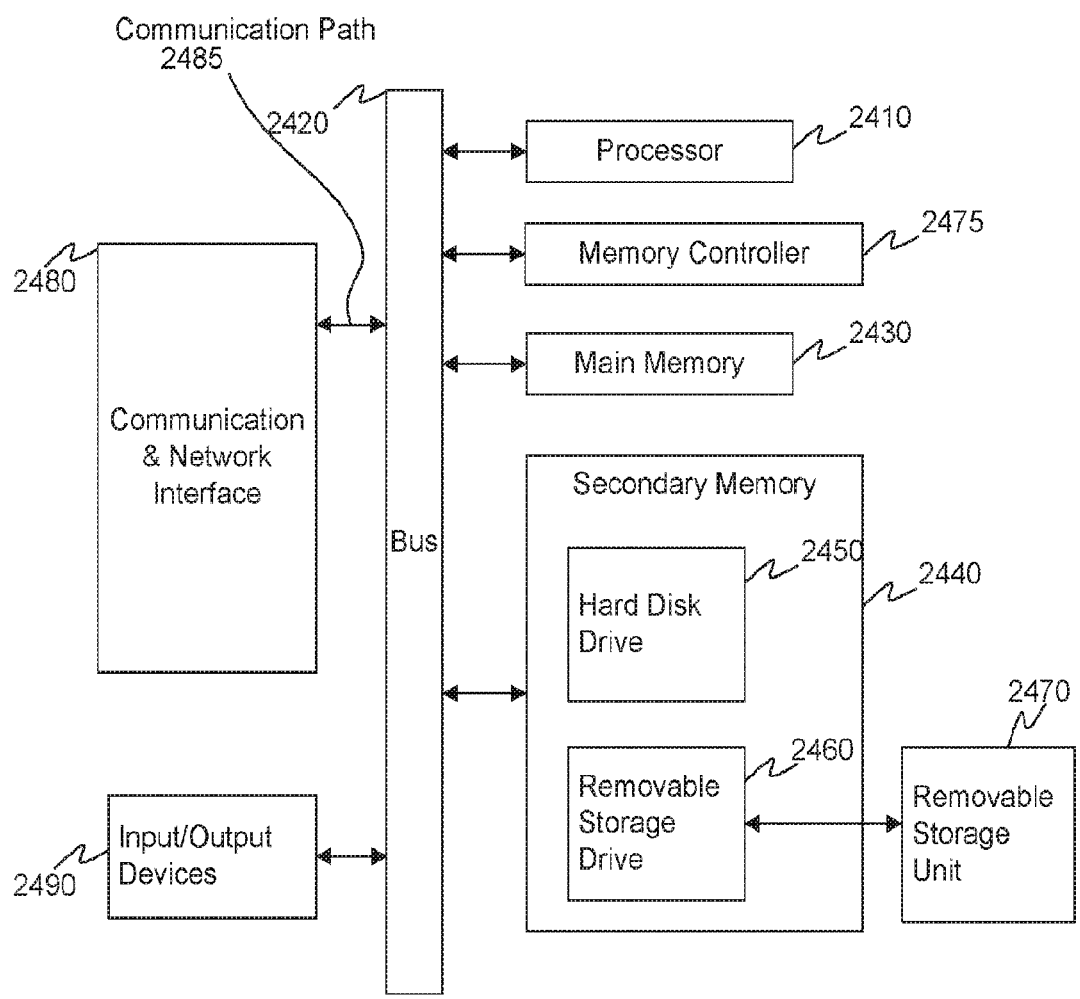
FIG. 24 illustrates an example computer system, according to an embodiment.

Various aspects of the disclosure can be implemented on a computing device by software, firmware, hardware, or a combination thereof. FIG. 24 illustrates an example computer system 2400 in which the contemplated embodiments, or portions thereof, can be implemented as computer-readable code. For example, the methods illustrated by flowcharts described herein can be implemented in system 2400. Various embodiments are described in terms of this example computer system 2400. After reading this description, it will become apparent to a person skilled in the relevant art how to implement the embodiments using other computer systems and/or computer architectures.

Computer system 2400 includes one or more processors, such as processor 2410. Processor 2410 can be a special purpose or a general purpose processor. Processor 2410 is connected to a communication infrastructure 2420 (for example, a bus or network). Processor 2410 may include a CPU, a Graphics Processing Unit (GPU), an Accelerated Processing Unit (APU), a Field-Programmable Gate Array (FPGA), Digital Signal Processing (DSP), or other similar general purpose or specialized processing units.

Computer system 2400 also includes a main memory 2430, and may also include a secondary memory 2440. Main memory may be a volatile memory or non-volatile memory, and divided into channels. Secondary memory 2440 may include, for example, non-volatile memory such as a hard disk drive 2450, a removable storage drive 2460, and/or a memory stick. Removable storage drive 2460 may comprise a floppy disk drive, a magnetic tape drive, an optical disk drive, a flash memory, or the like. The removable storage drive 2460 reads from and/or writes to a removable storage unit 2470 in a well-known manner. Removable storage unit 2470 may comprise a floppy disk, magnetic tape, optical disk, etc. which is read by and written to by removable storage drive 2460. As will be appreciated by persons skilled in the relevant art(s), removable storage unit 2470 includes a computer usable storage medium having stored therein computer software and/or data.

In alternative implementations, secondary memory 2440 may include other similar means for allowing computer programs or other instructions to be loaded into computer system 2400. Such means may include, for example, a removable storage unit 2470 and an interface (not shown). Examples of such means may include a program cartridge and cartridge interface (such as that found in video game devices), a removable memory chip (such as an EPROM, or PROM) and associated socket, and other removable storage units 2470 and interfaces which allow software and data to be transferred from the removable storage unit 2470 to computer system 2400.

Computer system 2400 may also include a memory controller 2475. Memory controller 2475 includes functionalities to control data access to main memory 2430 and secondary memory 2440. In some embodiments, memory controller 2475 may be external to processor 2410, as shown in FIG. 24. In other embodiments, memory controller 2475 may also be directly part of processor 2410. For example, many AMD™ and Intel™ processors use integrated memory controllers that are part of the same chip as processor 2410 (not shown in FIG. 24).

Computer system 2400 may also include a communications and network interface 2480. Communication and network interface 2480 allows software and data to be transferred between computer system 2400 and external devices. Communications and network interface 2480 may include a modem, a communications port, a PCMCIA slot and card, or the like. Software and data transferred via communications and network interface 2480 are in the form of signals which may be electronic, electromagnetic, optical, or other signals capable of being received by communication and network interface 2480. These signals are provided to communication and network interface 2480 via a communication path 2485. Communication path 2485 carries signals and may be implemented using wire or cable, fiber optics, a phone line, a cellular phone link, an RF link or other communications channels.

The communication and network interface 2480 allows the computer system 2400 to communicate over communication networks or mediums such as LANs, WANs the Internet, etc. The communication and network interface 2480 may interface with remote sites or networks via wired or wireless connections.

In this document, the terms "computer program medium," "computer-usable medium" and "non-transitory medium" are used to generally refer to tangible media such as removable storage unit 2470, removable storage drive 2460, and a hard disk installed in hard disk drive 2450. Signals carried over communication path 2485 can also embody the logic described herein. Computer program medium and computer usable medium can also refer to memories, such as main memory 2430 and secondary memory 2440, which can be memory semiconductors (e.g. DRAMs, etc.). These computer program products are means for providing software to computer system 2400.

Computer programs (also called computer control logic) are stored in main memory 2430 and/or secondary memory 2440. Computer programs may also be received via communication and network interface 2480. Such computer programs, when executed, enable computer system 2400 to implement embodiments as described herein. In particular, the computer programs, when executed, enable processor 2410 to implement the disclosed processes, such as the steps in the methods illustrated by flowcharts described above. Accordingly, such computer programs represent controllers of the computer system 2400. Where the embodiments are implemented using software, the software may be stored in a computer program product and loaded into computer system 2400 using removable storage drive 2460, interfaces, hard drive 2450 or communication and network interface 2480, for example.

The computer system 2400 may also include input/output/display devices 2490, such as keyboards, monitors, pointing devices, touchscreens, etc.

It should be noted that the simulation, synthesis and/or manufacture of various embodiments may be accomplished, in part, through the use of computer readable code, including general programming languages (such as C or C++), hardware description languages (HDL) such as, for example, Verilog HDL, VHDL, Altera HDL (AHDL), or other available programming and/or schematic capture tools (such as circuit capture tools). This computer readable code can be disposed in any known computer-usable medium including a semiconductor, magnetic disk, optical disk (such as CD-ROM, DVD-ROM). As such, the code can be transmitted over communication networks including the Internet. It is understood that the functions accomplished and/or structure provided by the systems and techniques described above can be represented in a scaffold that is embodied in program code and can be transferred to hardware as part of the production of integrated circuits.

The embodiments are also directed to computer program products comprising software stored on any computer-usable medium. Such software, when executed in one or more data processing devices, causes a data processing device(s) to operate as described herein or, as noted above, allows for the synthesis and/or manufacture of electronic devices (e.g., ASICs, or processors) to perform embodiments described herein. Embodiments employ any computer-usable or -readable medium, and any computer-usable or -readable storage medium known now or in the future. Examples of computer-usable or computer-readable mediums include, but are not limited to, primary storage devices (e.g., any type of random access memory), secondary storage devices (e.g., hard drives, floppy disks, CD ROMS, ZIP disks, tapes, magnetic storage devices, optical storage devices, MEMS, nano-technological storage devices, etc.), and communication mediums (e.g., wired and wireless communications networks, local area networks, wide area networks, intranets, etc.). Computer-usable or computer-readable mediums can include any form of transitory (which include signals) or non-transitory media (which exclude signals). Non-transitory media comprise, by way of non-limiting example, the aforementioned physical storage devices (e.g., primary and secondary storage devices).

While various embodiments of the present invention have been described above, it should be understood that they have been presented by way of example, and not limitation. It will be apparent to persons skilled in the relevant art that various changes in form and detail can be made therein without departing from the spirit and scope of the invention.

The present invention has been described above with the aid of functional building blocks and method steps illustrating the performance of specified functions and relationships thereof. The boundaries of these functional building blocks and method steps have been arbitrarily defined herein for the convenience of the description. Alternate boundaries can be defined so long as the specified functions and relationships thereof are appropriately performed. Any such alternate boundaries are thus within the scope and spirit of the claimed invention. One skilled in the art will recognize that these functional building blocks can be implemented by discrete components, application specific integrated circuits, processors executing appropriate software and the like or any combination thereof. Thus, the breadth and scope of the present invention should not be limited by any of the above-described exemplary embodiments, but should be defined only in accordance with the following claims and their equivalents.

What is claimed is:

1. A method for creating customized regenerative scaffolds, the method comprising:
   receiving a 3D image data set representing one or more teeth;
   displaying, on a user interface, an image of a tooth of the one or more teeth;
   receiving at least one user input;
   constructing a 3D root canal data set from the 3D image data set based on the at least one user input, wherein the 3D root canal data set represents a root canal having a physiologic apex;
   converting the constructed 3D root canal data set to control data for a computer controlled manufacturing system to manufacture the customized regenerative scaffold; and
   manufacturing, using the computer controlled manufacturing system, the customized regenerative scaffold based on the control data,
   wherein the customized regenerative scaffold comprises a body having a pre-formed contour that matches a contour of the root canal,
   wherein the customized regenerative scaffold is configured to fill the physiologic apex of the root canal, and
   wherein the customized regenerative scaffold is configured to promote tissue regrowth at the physiologic apex of the root canal.

2. The method of claim 1, further comprising transmitting the control data to the computer controlled manufacturing system configured to manufacture the customized regenerative scaffold using the control data.

3. The method of claim 1, wherein:
   the at least one user input comprises an indication of at least one of a physiologic apex and an orifice of the root canal of the tooth as displayed in the image, and
   the constructed 3D root canal data set is bounded by the at least one of the physiologic apex and the orifice of the root canal of the tooth as indicated by the at least one user input.

4. The method of claim 1, wherein the at least one user input comprises an indication of a type of treatment plan.

5. The method of claim 4, wherein the indication of the type of treatment plan indicates (a) a treatment plan in which no changes in geometry of the root canal will occur, (b) a treatment plan in which changes in geometry of the root canal will occur due to instrumentation using known instrumentation metrics, or (c) a treatment plan in which changes in geometry of the root canal will occur due to instrumentation without using known instrumentation metrics.

6. The method of claim 5, wherein:
   the indication of the type of treatment plan indicates the treatment plan in which changes in the geometry of the root canal will occur due to the instrumentation using the known instrumentation metrics, the known instrumentation metrics comprise an instrument size and an instrument shape selected from an instrument library, and
   the constructing comprises:
      retrieving a pre-constructed 3D instrument data set associated with the instrument size and the instrument shape; and
      constructing the 3D root canal data set from the 3D image data set based on the retrieved 3D instrument data set.

7. The method of claim 6, wherein the constructing the 3D root canal data set from the 3D image data set comprises:
   extracting a 3D data set representing a preoperative root canal of the tooth from the 3D image data set; and
   combining voxels of the 3D data set representing the preoperative root canal of the tooth and voxels of the retrieved 3D instrument data set to create the 3D root canal data set.

8. The method of claim 1, wherein the constructing the 3D output root canal data set comprises:
   constructing a 3D data set representing the root canal; and
   removing one or more outer layers of voxels of the 3D data set to construct the 3D root canal data set.

9. The method of claim 1, wherein the manufacturing comprises manufacturing the customized regenerative scaffold with one or more materials that promote transport of nutrients, oxygen, waste, or a combination thereof.

10. The method of claim 1, wherein the manufacturing comprises manufacturing the customized regenerative scaffold with a sterile material, an inert material, a biocompatible material, or a combination thereof.

11. The method of claim 1, wherein the manufacturing comprises manufacturing the customized regenerative scaffold with antimicrobial medicaments, antibiotic-eluting materials, macroparticles, nanoparticles, or a combination thereof.

12. The method of claim 1, wherein the manufacturing comprises manufacturing the customized regenerative scaffold with a support matrix or openings configured for cell organization, proliferation, differentiation, vascularization, or a combination thereof.

13. The method of claim 1, wherein the manufacturing comprises manufacturing the customized regenerative scaffold with one or more openings.

14. The method of claim 1, wherein:
   the computer controlled manufacturing system comprises a 3D printer; and
   the manufacturing comprises 3D printing the customized regenerative scaffold.

15. The method of claim 1, wherein the constructing the 3D root canal data set is based on at least one of pixel intensity values, Gaussian blurring values, and non-Gaussian blurring values of one or more areas of pixels enclosed in a region representing the root canal.

16. The method of claim 15, wherein the constructing the 3D root canal data set comprises automatically adjusting a long axis of the root canal to an angle such that a displayed region representing the root canal in a 2D reformation of the 3D image data set is larger than other displayed regions representing the root canal in the 2D reformation at other angles.

17. A system comprising memory and one or more processors coupled to the memory, the one or more processors configured to:
   receive a 3D image data set representing one or more teeth;
   display, on a user interface, an image of a tooth of the one or more teeth;
   receive at least one user input;
   construct a 3D root canal data set from the 3D image data set based on the at least one user input, wherein the 3D root canal data set represents a root canal having a physiologic apex;
   convert the constructed 3D root canal data set to control data for a computer controlled manufacturing system to manufacture a customized regenerative scaffold; and
   manufacture, using the computer controlled manufacturing system, the customized regenerative scaffold based on the control data,
   wherein the customized regenerative scaffold comprises a body having a pre-formed contour that matches a contour of the root canal,
   wherein the customized regenerative scaffold is configured to fill the physiologic apex of the root canal, and
   wherein the customized regenerative scaffold is configured to promote tissue regrowth at the physiologic apex of the root canal.

18. The system of claim 17, the one or more processors further configured to transmit the control data to the computer controlled manufacturing system configured to manufacture the customized regenerative scaffold using the control data.

19. The system of claim 17, wherein:
   the at least one user input comprises an indication of at least one of a physiologic apex and an orifice of the root canal of the tooth as displayed in the image, and
   the constructed 3D output root canal data set is bounded by the at least one of the physiologic apex and the orifice of the root canal of the tooth as indicated by the at least one user input.

20. The system of claim 17, wherein:
   the one or more processors are configured to construct the 3D root canal data set by displaying, on the user interface, a 2D reformation of the 3D image data set, wherein the 2D reformation comprises a reformatted image of the root canal of the tooth,
   the at least one user input comprises information associated with one or more areas of pixels enclosed in a region representing the root canal, as displayed in the 2D reformation, and
   the one or more processors are configured to construct the 3D root canal data set based on at least one of pixel intensity values, Gaussian blurring values, and non-Gaussian blurring values of the one or more areas.

21. The system of claim 20, the one or more processors further configured to, before the displaying the 2D reformation, automatically adjust a long axis of the root canal to an angle such that a displayed region representing the root canal in the 2D reformation is larger than other displayed regions representing the root canal in the 2D reformation at other angles.

22. The system of claim 17, wherein the one or more processors are configured to construct the 3D root canal data set by:
   constructing a 3D data set representing the root canal; and
   removing one or more outer layers of voxels of the 3D data set to construct the 3D root canal data set.

* * * * *